(12) United States Patent
Casscells, III et al.

(10) Patent No.: US 6,821,249 B2
(45) Date of Patent: Nov. 23, 2004

(54) TEMPERATURE MONITORING OF CONGESTIVE HEART FAILURE PATIENTS AS AN INDICATOR OF WORSENING CONDITION

(75) Inventors: Samuel Ward Casscells, III, Houston, TX (US); Saeed Payvar, Houston, TX (US)

(73) Assignee: Board of Regents, The University of Texas, Austin, TX (US)

( * ) Notice: Subject to any disclaimer, the term of this patent is extended or adjusted under 35 U.S.C. 154(b) by 70 days.

(21) Appl. No.: 10/247,667

(22) Filed: Sep. 19, 2002

(65) Prior Publication Data

US 2003/0092975 A1 May 15, 2003

Related U.S. Application Data

(63) Continuation-in-part of application No. 09/519,122, filed on Mar. 6, 2000, now Pat. No. 6,454,707.
(60) Provisional application No. 60/123,342, filed on Mar. 8, 1999.

(51) Int. Cl.[7] ................................................ A61B 5/00
(52) U.S. Cl. ........................ 600/300; 600/549; 128/898
(58) Field of Search ................................ 600/300–301, 600/549, 509, 485, 412, 474, 510, 513, 515, 582; 374/100, 109; 178/903, 920, 898; 607/9, 17–19, 21, 96

(56) References Cited

U.S. PATENT DOCUMENTS

| | | | |
|---|---|---|---|
| 4,216,462 A | 8/1980 | McGrath et al. | |
| 4,508,103 A | 4/1985 | Calisi | |
| 4,688,573 A | 8/1987 | Alt | |
| 4,726,383 A | 2/1988 | Cook et al. | |
| 4,763,112 A | 8/1988 | Hsieh | |
| 4,905,697 A | 3/1990 | Heggs et al. | |
| 4,922,930 A | 5/1990 | Adkins et al. | |
| 4,981,139 A | 1/1991 | Pfohl | |
| 5,005,574 A | 4/1991 | Fearnot et al. | |
| 5,050,612 A | 9/1991 | Matsumura | |
| 5,108,423 A | 4/1992 | Lu | |
| 5,241,965 A | 9/1993 | Mick | |
| 5,293,877 A | * 3/1994 | O'Hara et al. | 600/549 |
| 5,464,012 A | 11/1995 | Falcone | |
| 5,724,025 A | 3/1998 | Tavori | |
| 5,904,708 A | * 5/1999 | Goedeke | 607/18 |
| 5,964,701 A | 10/1999 | Asada et al. | |
| 6,045,513 A | * 4/2000 | Stone et al. | 600/508 |
| 6,190,324 B1 | * 2/2001 | Kieval et al. | 600/483 |
| 6,215,403 B1 | * 4/2001 | Chan et al. | 340/573.1 |
| 6,309,350 B1 | * 10/2001 | VanTassel et al. | 600/300 |
| 6,312,380 B1 | * 11/2001 | Hoek et al. | 600/437 |
| 6,368,284 B1 | 4/2002 | Brady | |
| 6,547,745 B1 | * 4/2003 | Rubinstein | 600/549 |
| 6,645,153 B2 | * 11/2003 | Kroll et al. | 600/481 |

OTHER PUBLICATIONS

Adams KF, Dunlap SH, Suteta CA, et al. Relation between gender, etiology and survival in patients with symptomatic heart failure. J Am Coll Cardiol. 1996; 28: 1781–1788.

Anastasiou–Nana MI, Nanas JN, Karagounis LA, et al. Relation of dispersion of QRS and QT in patients with advanced congestive heart failure to cardiac and sudden death mortality. Am J Cardiol. 2000; 85:1212–1217.

Anguita M, Arizon JM, Bueno G, et al. Clinical and hemodynamic predictors of survival in patients aged <65 years with severe congestive heart failure secondary to ischemic or nonischemic dilated cardiomyopathy. Am J Cardiol. 1993; 72: 413–417.

(List continued on next page.)

Primary Examiner—Mary Beth Jones
Assistant Examiner—Michael Astorino
(74) Attorney, Agent, or Firm—Tim L. Burgess, P.C.

(57) ABSTRACT

Indication of worsening health condition in patients with congestive heart failure using the analysis of the speed and pattern of temperature change in a way that is individualized toward patient's health condition.

102 Claims, 14 Drawing Sheets-

OTHER PUBLICATIONS

Anker SD, Ponikowski P, Varney S, et al. Wasting as independent risk factor for mortality in chronic heart failure. Lancet. 1997; 349: 1050–1053.

Astrup P, Engel K, Severinghaus JW, et al. The influence of temperature and pH on the dissociation curve of oxyhemoglobin of human blood. Scand J Clin Lab Invest. 1965; 17: 515–523.

Bart BA, Shaw LK, McCants CB, et al. Clinical determinants of mortality in patients with angiographically diagnosed ischemic or nonischemic cardiomyopathy. J Am Coll Cardiol. 1997; 30: 1002–1008.

Bittner V, Weiner DH, Yusuf S, et al. Prediction of mortality and morbidity with a 6–minute walk test in patients with left ventricular dysfunction. SOLVD Investigators. JAMA. 1993; 13: 1702–1707.

Blum A, Miller H. Pathophysiological role of cytokines in congestive heart failure. Annu Rev Med. 2001; 52: 15–27.

Brengelmann GL. Body temperature regulation in heart failure. Cardiologia. 1996; 41: 1033–1043.

Chomsky DB, Lang CC, Rayos GH, et al. Hemodynamic exercise testing: a valuable tool in the selection of cardiac transplantation candidates. Circulation. 1996; 94: 3176–3183.

Cohn JN, Levine TB, Olivari MT, et al. Plasma norepinephrine as a guide to prognosis in patients with chronic congestive heart failure. N Engl J Med. 1984; 311: 819–823.

Cohn JN, Rector TS. Prognosis of congestive heart failure and predictors of mortality. Am J Cardiol. 1988; 62: 25A–30A.

Cohn JN. Prognostic factors in heart failure: poverty amidst a wealth of variables. J Am Coll Cardiol. 1989; 14: 571–572.

Dargie HJ, Cleland JG, Leckie BJ, et al. Relation of arrhythmias and electrolyte abnormalities to survival in patients with severe chronic heart failure. Circulation. 1987; 75: IV98–IV107.

De Groote P, Millaire A, Foucher–Hossein C, et al. Right ventricular ejection fraction is an independent predictor of survival in patients with moderate heart failure. J Am Coll Cardiol. 1998; 32: 948–954.

Deng MC, De Meester JM, Smits JM, Heinecke J, Scheld HH. Effect of receiving a heart transplant: analysis of a national cohort entered on to a waiting list, stratified by heart failure severity. Comparative Outcome and Clinical Profiles in Transplantation (COCPIT) Study Group. BMJ. 2000; 321: 540–545.

Dries DL, Exner DV, Gersh BJ, et al. Atrial fibrillation is associated with an increased risk for mortality and heart failure progression in patients with asymptomatic and symptomatic left ventricular systolic dysfunction: a retrospective analysis of the SOLVD trials. J Am Coll Cardiol. 1998; 32: 695–703.

Francis GS, Cohn JN, Johnson G, et al. Plasma norepinephrine, plasma renin activity, and congestive heart failure: Relations to survival and the effects of therapy in V–HeFT II. The V–HeFT VA Cooperative Studies Group. Circulation. 1993; 87 (Suppl 6): V140–V148.

Gentilello LM, Jurkovich GJ, Stark MS, Hassantash SA, O'Keefe GE. Is hypothermia in the victim of major trauma protective or harmful! A randomized, prospective study. Ann Surg Oct. 1997; 226(4):439–47; discussion 447–9.

Givertz MM, Colucci WS. New targets for heart failure therapy: endothelin, inflammatory cytokines and oxidative stress. Lancet. 1998; 352(Suppl 1): S134–S138.

Gradman A, Deedwania P, Cody R, et al. Predictors of total mortality and sudden death in mild to moderate heart failure. Captopril–Digoxin Study Group. J Am Coll Cardiol. 1989; 14:564–570.

Gradman AH, Deedwania PC. Predictors of mortality in patients with heart failure. Cardiol. Clin. 1994; 12: 25–35.

Hallstrom A, Pratt CM, Greene HL, et al. Relations between heart failure, ejection fraction, arrhythmia suppression, and mortality: analysis of the Cardiac Arrhythmia Suppression Trial. J Am Coll Cardiol. 1995; 25: 1250–1257.

Hulsmann M, Stanek B, Frey B, et al. Value of cardiopulmonary exercise testing and big endothelin plasma levels to predict short–term prognosis of patients with chronic heart failure. J Am Coll Cardiol. 1998; 32: 1695–1700.

Jurkovich GJ, Greiser WB, Luterman A, Curreri PW. Hypothermia in trauma victims: an ominous predictor of survival. J Trauma Sep. 1987;27(9):1019–24.

Kihara T, Biro S, Imamura M, et al. Repeated sauna treatment improves vascular endothelial and cardiac function in patients with chronic heart failure. J Am Coll Cardiol. 2002; 39: 754–759.

Klingenheben T, Zabel M, D'Agostino RB, et al. Predictive value of T–wave alternans for arrhythmic events in patients with congestive heart failure. Lancet. 2000; 356: 651–652.

Lanfranchi PA, Braghiroli A, Bosimini E, et al. Prognostic value of nocturnal Cheyne–Stokes respiration in chronic heart failure. Circulation. 1999; 99: 1435–1440.

Lassvik CT, Areskog N. Angina in cold environment. Reactions to exercise. Br Heart J. Cohn JN, Ferrari R, Sharpe N. Cardiac remodeling—concepts and clinical Implications: a consensus paper from an international forum on cardiac remodeling. J Am Coll Cardiol. 2000; 35: 569–582, 1979; 42: 396–401.

Myers J, Gullestad L, Vagelos R, et al. Clinical, hemodynamic, and cardiopulmonary exercise test determinants of survival in patients referred for evaluation of heart failure. Ann Intern Med. 1998; 15: 286–293.

Packer M. Potential role of potassium as a determinant of morbidity and mortality in patients with systemic hypertension and congestive heart failure. Am J Cardiol. 1990, 65: 45E–52E.

Packer M. Sudden unexpected death in patients with congestive heart failure: a second frontier. Circulation. 1985; 72:681–685.

Parameshwar J, Keegan J, Sparrow J, et al. Predictors of prognosis in severe chronic heart failure. Am Heart J. 1992; 123: 421–426.

Poehlman ET, Scheffers J, Gottlieb SS, et al. Increased resting metabolic rate in patients with congestive heart failure. Ann Intern Med. 1994; 121: 860–862.

Rector TS, Cohn JN. Prognosis in congestive heart failure. Annu Rev Med. 1994; 45: 341–350.

Rodriguez–Garcia JL, Paule A, Dominguez J, et al. Effects of the angiotensin II antagonist losartan on endothelin–1 and norepinephrine plasma levels during cold pressor test in patients with chronic heart failure. Int J Cardiol. 1999; 70: 293–301.

Shellock FG, Swan HJ, Rubin SA. Muscle and femoral vein temperatures during short–term maximal exercise in heart failure. J Appl Physiol. 1985; 58: 400–408.

Shibutani K, Komatsu T, Kubal K, Sanchala V, Kumar V, Bizzarri DV. Critical level of oxygen delivery in anesthetized man. Crit Care Med Aug. 1983;11 (8):640–3.

Siddiqui H, Patel S, Lal BN, et al. Hypothermia: a new indicator of imminent death in congestive heart failure. J Am Coll Cardiol. 1999; 33: 212A.

Szlachic J, Massie BM, Kramer BL, et al. Correlates and prognostic implications of exercise capacity in chronic congestive heart failure. Am J Cardiol. 1986; 55: 1037–1042.

Tei C, Horikiri Y, Park JC, et al. Acute hemodynamic improvement by thermal vasodilation in congestive heart failure. Circulation. 1995; 91: 2582–2590.

Tsuji H, Larson MG, Venditti FJ, et al. Impact of reduced heart rate variability on risk for cardiac events. The Framington Heart Study. Circulation. 1996; 94: 2850–2855.

Tsutamoto T, Hisanaga T, Wada A, et al. Interleukin–6 spillover in the peripheral circulation increases with the severity of heart failure, and the high plasma level of interleukin–6 is an important prognostic predictor in patients with congestive heart failure. J Am Coll Cardiol. 1998; 31: 391–398.

Weg JG. Oxygen transport in adult respiratory distress syndrome and other acute circulatory problems: relationship of oxygen delivery and oxygen consumption. Crit Care Med May 1991;19(5):650–7.

Westheim A, Os I, Thaulow E, et al. Haemodynamic and neurohumoral effects of cold pressor test in severe heart failure. Clin Physiol. 1992, 12: 95–106.

Whittle JL, Bates JH. Thermoregulatory failure secondary to acute illness: complications and treatment. Arch Intern Med. 1979, 139: 418–421.

* cited by examiner

ROC for T

TEMPERATURE MONITORING OF CONGESTIVE HEART FAILURE PATIENTS AS AN INDICATOR OF WORSENING CONDITION

CROSS REFERENCE TO RELATED APPLICATIONS

This application is a continuation-in-part of U.S. patent application Ser. No. 09/519,122, filed Mar. 6, 2000 now U.S. Pat. No. 6,454,707, which claims priority to U.S. provisional patent application 60/123,342, filed Mar. 8, 1999.

STATEMENT REGARDING FEDERALLY SPONSORED RESEARCH OR DEVELOPMENT

The U.S. Government has a paid-up license in this invention and the rights in limited circumstances to require the patent owner to license others on reasonable terms as provided for by the terms of Grant No. DAMD17-98-1-80002 awarded by U.S. Army Medical Research Acquisition Activity.

BACKGROUND OF THE INVENTION

1. Field of the Invention

The present invention generally relates to apparatus and methods for continuous monitoring of health condition in patients with congestive heart failure.

2. Background Information

Congestive heart failure ("CHF") is a chronic inability of the heart to maintain an adequate output of blood from one or both ventricles of the heart to meet the metabolic demands of the tissues. With a markedly weakened left ventricle or right ventricle or both, the volume of blood presented to the heart is in excess of the heart's capacity to move it along. Consequently, fluid builds up behind the heart. With a weakened left ventricle or right ventricle or both, there is a shift of large volumes of blood from the systemic circulation into the pulmonary (lung) circulation. If the inability to move the volume of blood forward is due to a left heart problem without the right side failing as well, blood continues to be pumped into the lungs by the normal right heart, while it is not pumped adequately out of the lungs by the left heart. As the volume of blood in the lungs increases, the pulmonary vessels enlarge, pulmonary venous congestion develops, and, once the pulmonary capillary pressure rises above a critical point, fluid begins to filter out of the capillaries into the interstitial spaces and alveoli (air sacs in the lungs where exchange of oxygen and carbon dioxide occurs), resulting in pulmonary edema. Subsequently this can lead to pleural effusion (effusion is the escape of fluid into a part) and abdominal effusion. If the abnormality lies in the right heart or the pulmonary arteries, limiting the ability to move blood forward, then congestion occurs behind the right heart (causing pleural effusion and/or build up of fluid in the abdomen).

CHF is the fourth leading cause of death in the United States and a leading cause of poor quality of life in the population over 65. There are 5 million cases of CHF in the United States. In patients diagnosed with CHF, sudden cardiac death occurs at 6 to 9 times the rate of the general population. A 44 year follow-up Framingham Heart Study of the National Heart, Lung and Blood Institute (the "NHLBI", part of the U.S. National Institute of Health), has found, based on hospital admissions, that there are nearly 550,000 admissions of new cases of CHF each year in the United States. The number of patients hospitalized for CHF annually is 1.01 million. CHF approaches 10 cases per 1000 members of the U.S. population after age 65. CHF hospitalizations have increased steeply in the last 20 years, the number of hospital discharges (which includes both the living and the dead) more than doubling both for males and females from 1979 to 1999. As the population of 65 and older grows hugely in the U.S. with the aging of the baby boomer generation, and as the number of first heart attack survivors increases, CHF portends a dramatic increase of morbidity and mortality and a burgeoning drain on healthcare funds in the U.S.

One of many needs for CHF patients is accurately predicting when they have a significantly worsening condition signifying death draws near. With sufficient warning, steps can be taken to save them. Among CHF patients in the very poorest condition, there is a need to know which patients are likely to have the shortest lives in order to select those for whom heart transplantation or left ventricular assist device (LVAD) implantation is the appropriate treatment.

Bedside classifiers such as age, sex, ischemic heart disease (IHD), cardiac cachexia, and New York Heart Association (NYHA) functional classes for CHF are useful factors for general prognosis of risk of poor outcome, but do not provide physiologically specific or dynamic information. With today's sophisticated medical diagnostics technology, especially in large urban medical center complexes, much can be done in a hospital environment to develop specific test information concerning the condition of a patient's heart. Numerous predictors of mortality in patients with CHF have been described in the literature. Some of the tests that can be performed include, without limitation: chest wall impedance, chest impedance peak oxygen uptake (dot(V) O2), left and right ventricular ejection function (LVEF and RVEF), both respiratory and circulatory response to exercise (exercise capacity, especially if combined with maximal oxygen consumption), cardiac index, left ventricular cavity size, left ventricular stroke work index, right and left ventricular filling pressure (RVFP and LVFP) and isovolumic relaxation time (LV IVRT), left ventricular systolic pressure (LV SP), right and left atrial pressure, systemic vascular resistance, calculated wall stress, tricuspid regurgitation (TR), jugular venous pressure (JVP), pulmonary capillary wedge pressure (PCWP), 6-minute walk distance, arterial and venous pH, pO2, pCO2, serum creatinine, serum sodium, plasma norepinephrine, plasma neurotensin, plasma renin activity (PRA), plasma arginine vasopressin, plasma atrial and brain natriuretic peptides, plasma endothelin-1, plasma interleukin-6, plasma tumor necrosis-alpha, serum sodium, serum potassium (and total potassium stores), serum magnesium, lymphocyte count, frequent ventricular extrasystoles, ventricular tachycardia (VT), bundle-branch blockage (left and right), atrial fibrillation or flutter, T-wave alternans, QT prolongation and dispersion, $PACO_2$, pH, respiratory rate, QRS width, R—R variability, and dP/dt. Quite surprisingly, however, these heart performance or heart condition factors together account for only a portion of statistical variance as a predictor of poor outcome in CHF patients, usually applying to only a few patients, leaving prognosis uncertain for the individual patient.

Even these tests don't help much if the patient isn't hospitalized to receive them at a critical time. Home-monitoring promises an opportunity to reduce costs and improve quality of life in some patients. Prognostic variables described in the literature that might be readily monitored at home include S3 gallop, Cheyne-Stokes respiration, apnea/hypopnea index, systolic blood pressure (SBP), heart rate at rest (HR), pulse pressure (PP), and mean arterial pressure (MAP). However, these factors are not statistically strong predictors of risk of imminent death.

SUMMARY OF THE INVENTION

Our invention involves detecting a significant worsening of condition of a CHF patient and issuing an alert so that life saving therapies and interventions can be summoned to save the patient's life and/or intervention devices can be activated or adjusted. In an aspect of the invention, the output of an alert is to a medical device that applies a therapeutic treatment to the patient to treat the patient's condition of congestive heart failure. The device suitably may be a ventricular assist device responsive to the alert to provide additional ventricular assist to the patient. The device may be an medication release device responsive to the alert to adjust the amount of medication the patient is receiving. Or the device may be a cardiac rhythmic regulator, such as a pacemaker or defibrillator, responsive to the alert to optimize the patient's regulator parameters to reverse hypothermia, or a device responsive to the alert to warm the patient.

In a significant departure from use of other prognostic factors, these new methods and apparatus not only are dynamically predictive but also are applicable for watching the individual patient on an ambulatory and continuous basis, allowing the patient to be monitored at home or elsewhere as well as in-hospital. This allows the patient an improved quality of life yet protects the patient by enabling immediate availability of professional care appropriate to his or her condition for timely initiated therapy or intervention.

In the parent application of which this is a continuation in part, there is described the discovery that very mild hypothermia is an indicator of imminent death in CHF patients. Hypothermia is generally defined as a core body temperature of 35° C. (95° F.) or below and is classified as mild (35–32° C.; 95–89.2° F.), moderate (<32 to 28° C.; <89.2–82.4° F.), or severe (<28° C.; <82.4° F.). See Petty, K. J., "Hypothermia", in CARDINAL MANIFESTATIONS AND PRESENTATION OF DISEASES, McGraw-Hill Companies, 1998.

In continuing this investigation, we have now discovered that rate of fall of temperature of a CHF patient varies insignificantly compared to single temperature measurements at admission or at any time during hospitalization, and that, accordingly, rate of temperature fall provides a primary and sensitive measure for prediction of imminent death that can prompt issuance of an alert for life saving steps to be timely initiated.

In accordance with our discovery, our invention includes methods, means, apparatus and systems for continuously monitoring a CHF patient against a cut-off point set for rate of fall of body temperature as at least one temperature attribute of the very mild hypothermia that is an indicator of imminent death in CHF patients.

The method, means, apparatus and systems alert a worsening of condition in a patient with congestive heart failure, in operations which comprise (a) pre-setting a cut-off point of at least one temperature attribute of hypothermia comprising rate of fall of body temperature relative to optimum sensitivity and specificity for such attribute as a congestive heart failure predictor of death of a patient, (b) routinely determining that attribute in the patient, (c) determining from the routine determinations of the attribute whether a condition of congestive heart failure hypothermia has occurred, and if so, (d) issuing an alert warning of the worsening condition.

In one aspect operation, (c) comprises determining whether the attribute has attained or crossed the cut-off point. In another aspect in which the invention comprises routinely determining the attribute for at least one peripheral site and for a core site, operation (c) comprises determining whether the attributes in both the sites are moving in the direction of the cut-off point. In another aspect, operation (c) comprises determining whether rise of core temperature of the patient from a temperature below a baseline temperature of the patient to a temperature at or closer to baseline lags behind rise of core temperature of the normal person from a temperature below a baseline temperature of the normal person to a temperature at or closer to baseline, or if the core temperature of the patient rises from a temperature below a baseline temperature of the patient to less than a predetermined minimum acceptable rise.

In an embodiment of our invention, the cut-off point is set relative to optimum sensitivity and specificity for rate of fall of body temperature as at least one temperature attribute of hypothermia as a congestive heart failure predictor of death of a patient. That attribute is periodically determined in the patient, and that attribute is reckoned for whether it has attained or crossed the cut-off point set for that attribute, and if so, an alert is issued.

In addition to at least rate of fall of body temperature as one temperature attribute of hypothermia as a congestive heart failure predictor of death of a patient, the attribute also may be a hypothermic body temperature of the patient, amount of body temperature fall in a selected interval, the interval's duration, and the frequency of such intervals.

By setting the cut-off point relative to optimum sensitivity and specificity for rate of fall of body temperature, the invention enables customizes the alarming system toward the specific health condition and needs of the patient. The system alarms sooner if the patient is in an otherwise poorer prognostic category, suffers other mental/health disabilities, or is located away from healthcare. This presetting, which is done by the health care professional that oversees the functionality of the device, or which in certain instances may be increased automatically, is based on (1) the patient's other co-morbidities; (2) other prognostic factors; and (3) the time and distance availability of professional and/or nonprofessional healthcare.

Our invention also includes, in additional aspects and embodiments, personalization to the CHF patient's own baseline temperature set-point, and personalization also to circadian and lunar changes in temperature of the patient. In another enhancement, the invention further comprises determining and making adjustments to periodically determined temperature attributes to take into account external factors, such as one or more environmental factors to which the patient is exposed, for example, temperature and light, and to take into account internal factors such as the patient's activity, medications, smoking, alcohol use, or other factors that can affect the patient's body temperature, such as hot or cold solid and/or fluid intake.

Another embodiment of our invention involves routinely determining a temperature attribute for at least one peripheral site and for a core site and determining whether that attribute in both such sites is moving in the direction of the cut-off point, and if so, outputting an alert. Temperature is measured both on the surface of the patient and at a location providing a core temperature, and watch is made for both low or falling core temperatures and low or falling surface temperatures (or both low and failing surface and core temperatures). Occurrence of a low or falling surface temperature at a time when baseline temperature stays normal may signify nothing more than exposure to a cold environment; or the patient's having Raynaud's disease, a condition in which peripheral circulation is impaired in the extremities. However, occurrence of low or falling surface temperatures coupled with low or falling core temperature is an ominous indication that heat is transferring from the core to the exterior surface where coldness indicates it is being lost with terminal consequences.

In another embodiment there is provided method and means for monitoring and warning of worsening of condition of congestive heart failure in a patient, which comprises monitoring and recording environmental temperature and core temperature of the patient and determining whether a steep fall in environmental temperature has occurred. If so, the patient's core temperature and the patient's change in core temperature over time is compared to a core temperature and a change in core temperature over time of a normal person at environmental temperatures monitored beginning with the temperatures included in the steep fall. An alert is issued if rise of core temperature of the patient, from a temperature below a baseline temperature of the patient to a temperature at or closer to baseline, lags behind rise of core temperature of the normal person from a temperature below a baseline temperature of the normal person to a temperature at or closer to baseline. An alert is alternatively issued if the core temperature of the patient rises from a temperature below a baseline temperature of the patient to less than a predetermined minimum acceptable rise.

These and numerous other aspects of our invention are described in detail below, including with reference in part to illustrations that are now described.

DETAILED DESCRIPTION OF INVENTION

Figure 1:
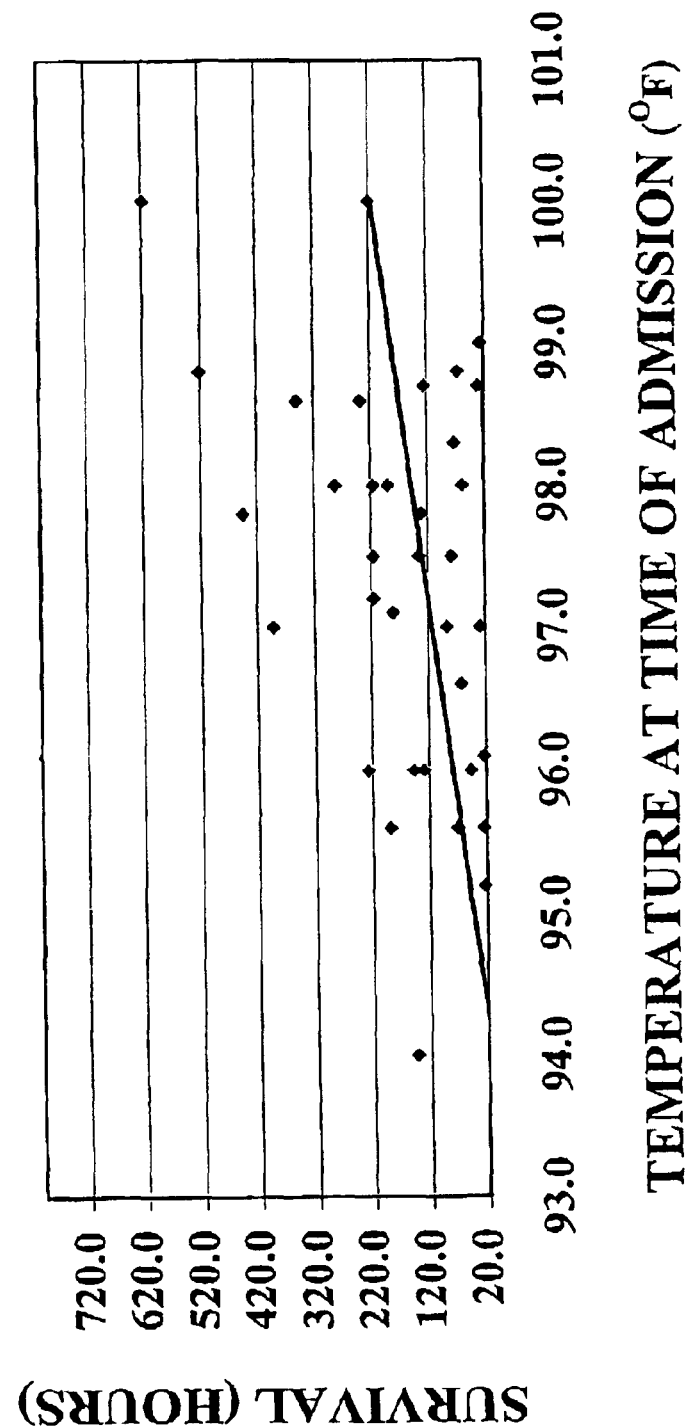
FIG. 1 is a graph illustrating that the temperature of a congestive heart failure patient upon admission into the hospital is predictive of that patient's survival.

Initially, as described in the patent application of which this is a continuation-in-part, it was observed that one patient's temperature (T) fell from 97° F. to 91.7° F. two hours prior to death from severe congestive heart failure despite maintenance of normal heart rate, blood pressure and mentation. A similar situation was noted in two more patients. In the third patient, medical treatment (nitrates, enalopril, digoxin) was intensified, the patient was warm, and the patient survived. This led to the novel hypothesis that some patients become hypothermic prior to death from congestive heart failure. This hypothesis was in contrast to teachings in the field suggesting that CHF is characterized by normal and slightly elevated temperatures.

Hypothermia was investigated as an indicator of imminent death from congestive heart failure. The outcomes of a number of patients admitted to the hospital with a diagnosis of congestive heart failure were investigated to correlate their body temperature with death. The Department of Medical Records at Hermann Hospital in Houston, Tex., USA, was the source of the data reported herein. A case-control retrospective study of patients who were admitted with CHF as one of the principal diagnoses was performed. The diagnosis was in accordance with the International Classification of Diseases, 9th Revision, Clinical modification (ICD-9 CM). Information about CHF admissions, deaths, and discharges between Jan. 1, 1996 until Jun. 1, 1998 were collected. The cases were selected on the basis of having pure CHF without any other condition known to affect temperature. Exclusion criteria included all the deaths and discharges that were complicated with temperature confounders such as hepatic failure, infections, acute stroke, sepsis, thyroid disease, alcohol intoxication, exposure to cold or heating blankets. Medications were not causes for exclusion (non-steroidal anti-inflammatory drugs, such as aspirin or acetaminophens; steroids; vasopressors). Cardiovascular diseases were not causes for exclusion.

Patients who died were selected as cases and were divided into two groups; those who died with hypothermia and those who died without it. Controls were randomly selected patients discharged alive with CHF as a primary diagnosis who fulfilled the same inclusion criteria as the cases. Controls were divided into two groups in a manner identical to the cases (i.e., those having hypothermia and those without hypothermia). Overall 148 patients (53 cases and 95 controls) were analyzed by SPSS software (1998). Table 1 gives patient demographics of cases (deaths) and controls (patients discharged alive with CHF) and univariate analysis of differences (2-tailed P; equal variances assumed). Patients who died of CHF had lower systolic blood pressure, serum sodium, leukocyte count and higher creatinine. Age and diastolic blood pressure were borderline predictors.

TABLE 1

Univariate Analysis

| Variables | Cases (N = 53) | Controls (N = 96) | P Value |
|---|---|---|---|
| Age (Years) | 73.45 +/− 13.8 | 69.3 +/− 14.3 | 0.088 |
| Sex (M:F) | 24:29 | 52:44 | |
| Race (W, B, O) | W: 29, B: 19, O: 05 | W: 41, B: 46, O: 4, H: 5 | |
| Systolic BP | 118.4 +/− 28.1 | 136.9 +/− 26.7 | 0.0001 |
| Diastolic BP | 70 +/− 17.5 | 75.7 +/− 17.5 | 0.060 |
| HR | 88.1 +/− 21.9 | 84.6 +/− 19.9 | 0.320 |
| Creatinine (Cr) | 1.9 +/− 1.4 | 1.4 +/− 1.1 | 0.014 |
| Sodium (Na) | 137.9 +/− 3 | 138 +/− 3.2 | 0.941 |
| LVEF (%) | 37 +/− 17.7 | 42.4 +/− 14.9 | 0.364 |
| RVF | ↓↓ | ↓ | |
| Leukocytes (WBC's) | 8.8 +/− 2.1 | 8.1 +/− 1.8 | 0.022 |
| Lymphocyte Count | 15 +/− 6.8 | 20.1 +/− 9.3 | 0.001 |
| Last Temp (T2) | 96.5 +/− 2.3 | 97.6 +/− 0.9 | 0.0001 |
| Adm. Temp (T1) | 97.2 +/− 1.8 | 97.7 +/− 0.8 | 0.025 |
| Ave. Temp | 97.1 +/− 1.5 | 97.6 +/− 0.7 | 0.003 |
| T ↓ (last 12 hrs) | −0.6 +/− 1.9 | −0.01 +/− 1.0 | 0.009 |
| ΔT (T2 − T1) | −0.7 +/− 2.7 | −0.1 +/− 1.1 | 0.066 |

As seen from Table 1, the most significant predictors were the last recorded oral temperature, lymphocyte count, temperature fall over the last 12 hours, average temperature and admission temperature.

A multivariate logistic regression analysis of the data was conducted. Table 2 gives the multivariate logistic regression analysis of variables of systolic blood pressure (SBP), creatinine (CR), leukocyte count (WBC), lymphocyte count (lymph), last temperature (temp, indicating the last recorded temperature divided categorically into $\geq 97°$ F. and $<97°$ F.) and diastolic blood pressure (DBP). Variables with a P value above 0.1 in the univariate analysis were not included. The odds ratio and 95% confidence intervals are shown.

TABLE 2

Multivariate Logistic Regression Analysis

| Variable | Odds Ratio | 95% CI | P Value |
|---|---|---|---|
| Systolic Blood Pressure | 0.972 | 0.94–0.99 | 0.042 |
| Diastolic Blood Pressure | 1.023 | 0.98–1.06 | 0.247 |
| Creatinine | 1.570 | 1.10–2.23 | 0.011 |
| Leukocytes | 1.343 | 1.04–1.71 | 0.019 |
| Lymphocyte Count | 0.920 | 0.86–0.97 | 0.005 |
| Last Temp | 10.254 | 3.74–28.10 | 0.00001 |

The strongest predictor of death during the patient's hospital stay was the last recorded oral temperature, followed by the lymphocyte count. In this case-control study, hypothermia emerged as a strong predictor of death in patients admitted with congestive heart failure.

This was surprising because temperature is not listed as a prognostic variable in any of the dozen of papers on or about prognosis of CHF. Indeed, it had not even been included in the data sets. Nor is CHF listed as a cause of hypothermia though age, stroke, medications and shock which often coexists with CHF are known risks for hypothermia. Therefore, a second study was undertaken to see if the first could be confirmed.

Because case-control studies have well-known limitations, including missing data, and can be confounded by unsuspected associations, a second type of study was performed, a retrospective cohort study. All of the 1998 admissions to Hermann Hospital whose primary discharge diagnosis (or death) was congestive heart failure were analyzed, using the same International Classification of Disease coding as in the previous study. For patients admitted more than once during the year, only the last admission was studied. Potential confounders of temperature, such as sepsis, acute stroke, thyroid disease, alcohol intoxication or cold exposure, resulted in the exclusion of 35 of an original 423 patients; medications were not used to exclude patients. Another 97 were excluded because of multiple admissions to the hospital during that year. The remaining 291 charts were reviewed according to the following prospective criteria, which include the reported prognostic variables for CHF, in groupings that conform to the usual stages of clinical assessment of the patient. Analysis was done using the Cox regression method.

Bedside variables were considered first. These included age, sex, a history of hypertension or diabetes or coronary artery disease or symptoms thereof, New York Heart Association (NYHA) CHF class, valvular disease, heart rate, blood pressure and temperature. In situations of missing data, the variable was dropped if more than a third of the patients were lacking that particular variable. Of the remaining variables, missing data were handled by assuming the mean of the cohort for that particular variable.

A second analysis examined the prognostic ability of admission temperature compared to arrhythmia (ventricular tachycardia and/or atrial fibrillation) and RR variability. No analysis for T-wave alternans was undertaken because arrhythmic death was not the focus of the study.

A third analysis compared temperature to echocardiographic and angiographic variables.

A fourth analysis compared temperature to laboratory variables, including creatinine, serum sodium, lymphocyte count, glucose, potassium and carbon dioxide.

In the comparison of bedside variables (shown in Table 3), hypothermia was the best predictor of in-hospital mortality (P=0.004), followed by systolic blood pressure (P=0.015) NYHA class (P=0.47) and female sex (P=0.047). Tricuspid regurgitation showed a trend toward significance (P=0.06), but hypertension, diabetes, coronary artery disease, diastolic BP, mitral regurgitation and heart rate on admission did not.

TABLE 3

Multivariate analysis of bedside variables (derived from history and exam) predicting in-hospital mortality of CHF patients.

| Variable | Odds Ratio | P Value |
|---|---|---|
| Temperature | 0.3296 | 0.0042 |
| Sex (Female) | 3.6733 | 0.0468 |
| NYHA | 2.3920 | 0.0469 |
| TR | 31.6312 | 0.0604 |
| SBP | 0.9561 | 0.0154 |

Temperature is mean of hospital stay;
NYHA = New York Heart Association;
CHF = Congestive Heart Failure;
TR = Tricuspid valve regurgitation;
SBP = Systolic Blood Pressure on admission.
Variables not associated with mortality were age, history of hypertension, diabetes, or coronary atherosclerosis; findings of aortic or mitral valve disease, heart rate, and diastolic blood pressure.

Compared to electrocardiographic variables, such as arrhythmia and variability in the RR interval (P=0.88 and 0.89, respectively), temperature was more significant, with a borderline P value of 0.06. Most charts lacked an LVEF or RV dimension for that specific hospitalization. Analysis of just those cases that did have the data revealed that, compared to LVEF, temperature was of borderline significance (OR=0.45, P=0.06) while LVEF was not a significant predictor (P=0.77). However, among cases with data on RV enlargement (OR=8.8, p=0.014), temperature lost predictive value. This must be interpreted with caution because it is a subset analysis (only 2 variables) on a subset of patients (96 of 291) that may have a selection bias. In any event RV function cannot be evaluated at the bedside or monitored non-invasively.

Compared to laboratory variables, temperature was of borderline significance (P=0.077), and creatinine, a well-recognized prognostic factor, was the most significant, with a P value of 0.003. In this data set, hyponatremia and lymphopenia were not significant (P=0.53 and P=0.70, respectively). Bilirubin, a recently described predictor, was not measured in enough patients to be included in the multivariate analysis. In a subset analysis of 193 patients, T remained predictive (OR=0.32, P=0.0008) but bilirubin (P=0.27) was not.

Other variables with too many missing data points for inclusion in the multivariate analysis, which were compared in subset analyses to temperature were VT (OR=8.7, p=0.0000, vs. OR=0.44, p=0.046 for T) and variables which did not predict mortality (AF, R—R variability, and use of beta-blockers, ACE inhibitors, aspirin, or amiodarone) though in each comparison T remained significantly and inversely associated with mortality.

Figure 2:
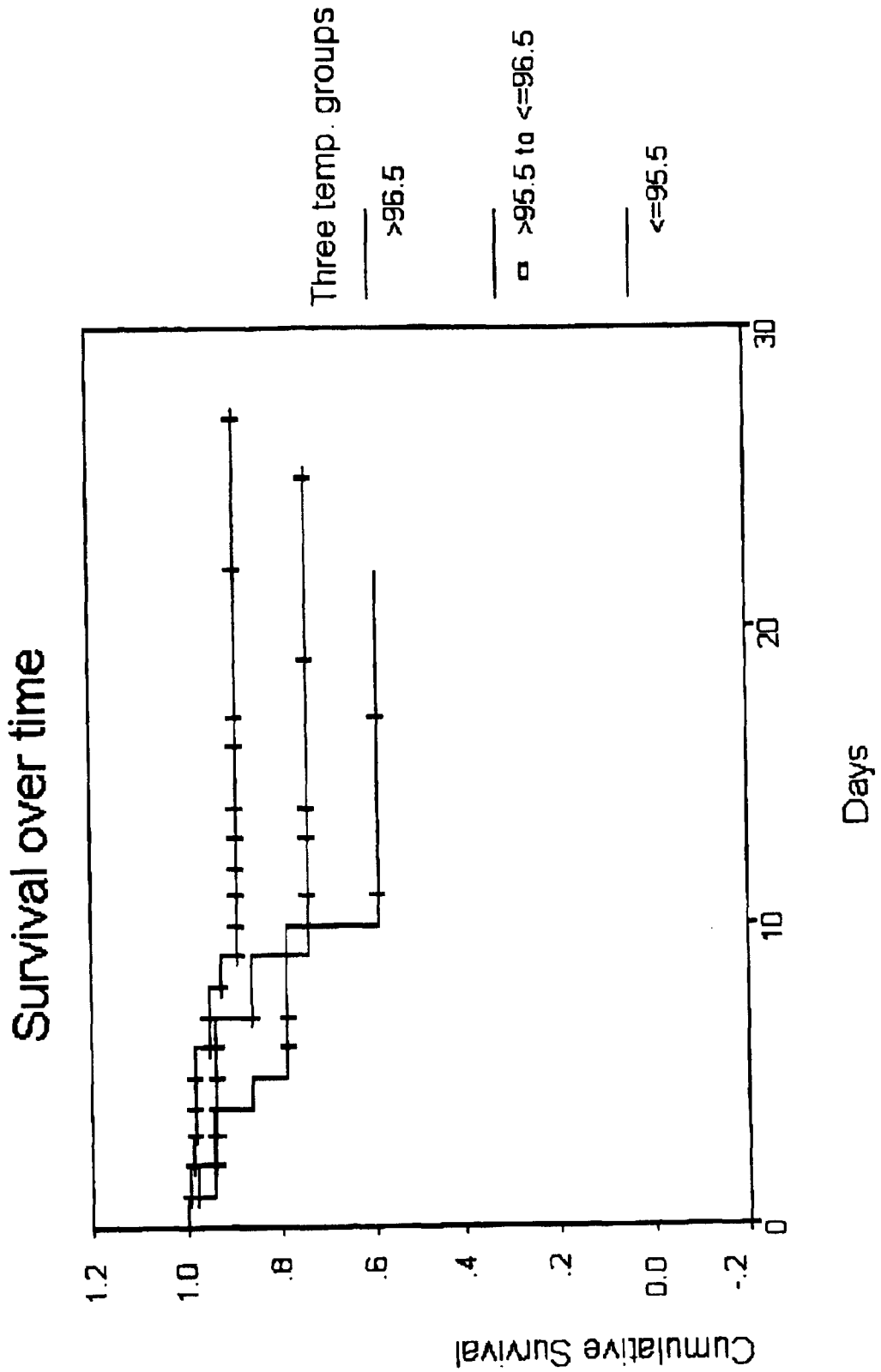
FIG. 2 is a graph of cumulative survival of the same data group as used in FIG. 1 vs. number of days of survival for three temperature subsets, those in which temperature on admission was greater than 96.5° F., those in which temperature on admission was between 95.5 and 96.5° F., and those for whom temperature at admission was less than 95.5° F.

Taken together, these different analyses of different data sets demonstrate with considerable consistency an association of hypothermia with CHF mortality. The data, derived from two different types of analysis, are robust. Admission temperature, shown in Table 1 with a P value of 0.025, was also shown to correlate with survival. FIG. 1 plots the temperature at the time of admission against the survival time of the patient in hours. As can be seen in the graph shown in FIG. 1, temperature at the time of admission is related to the patient's survival time. Moreover, a core temperature decrease from the patient's baseline temperature (e.g., average temperature or temperature upon admission to the hospital) is predictive of imminent death in the patient (i.e., within 24 hours) and suggests that the patient needs more intensive medical therapy or consideration for heart transplantation or left ventricular assistance. Hypothermia as a predictor of imminent death in late stage CHF is further illustrated in FIG. 2, which is a plot of cumulative survival of the same data group as FIG. 1, verses number of days of survival for three temperature groups, those in which temperature on admission was greater than 96.5° F., those in which temperature on admission was between 95.5 and 96.5° F., and those for whom temperature at admission was less than 95.5° F.

Continuing the investigation described in the parent of which this is a continuation-in-part, using a nested case-control design, a cohort of 291 patients [age 73 years ±13 (SD), 154(53%) women] was studied, chosen from 326 patients who were admitted with an ICD-9 CM principle diagnosis of CHF to the Memorial Hermann Hospital in Houston, Tex., during the period of January to December of 1998 after excluding 35 patients with conditions known to confound temperature. Speed of temperature change during a certain time period was calculated as the amount of temperature difference in ° F. between any reading at a certain point in time and the previous reading divided by the number of hours between the two. During a mean hospital stay of 5 days ±4 (SD), 5136 temperature points had been recorded (oral, rectal, aural or bladder) which yielded an average of 17 speed of temperature change measurements per patient (about 3 per day, generally corresponding to temperatures being taken once during each of three 8 hour nursing shifts). The results are set forth in Table 4.

TABLE 4

Sensitivity and specificity for speed of temperature change as predictor of death

| Cutoff (° F.) | Specificity | Sensitivity | CI95% Specificity | | CI95% Sensitivity | |
|---|---|---|---|---|---|---|
| −1.20 | 0.9891 | 0.1765 | 0.9771 | 1.0010 | 0.1327 | 0.2203 |
| −1.10 | 0.9891 | 0.1765 | 0.9771 | 1.0010 | 0.1327 | 0.2203 |
| −1.00 | 0.9854 | 0.1765 | 0.9716 | 0.9992 | 0.1327 | 0.2203 |
| −0.90 | 0.9745 | 0.1765 | 0.9563 | 0.9926 | 0.1327 | 0.2203 |
| −0.80 | 0.9526 | 0.1765 | 0.9281 | 0.9770 | 0.1327 | 0.2203 |
| −0.70 | 0.9307 | 0.1765 | 0.9015 | 0.9598 | 0.1327 | 0.2203 |
| −0.60 | 0.8431 | 0.1765 | 0.8013 | 0.8849 | 0.1327 | 0.2203 |
| −0.50 | 0.6971 | 0.4118 | 0.6443 | 0.7499 | 0.3552 | 0.4683 |
| −0.40* | 0.5876 | 0.5294 | 0.5310 | 0.6442 | 0.4721 | 0.5868 |
| −0.30 | 0.3869 | 0.7059 | 0.3309 | 0.4428 | 0.6535 | 0.7582 |
| −0.20 | 0.1788 | 0.7647 | 0.1348 | 0.2229 | 0.7160 | 0.8134 |
| −0.10 | 0.0292 | 0.9412 | 0.0099 | 0.0485 | 0.9141 | 0.9682 |
| 0.00 | 0.0036 | 0.9412 | −0.0033 | 0.0106 | 0.9141 | 0.9682 |

(*Bolded figures show optimal sensitivity and specificity.)

Figure 3:
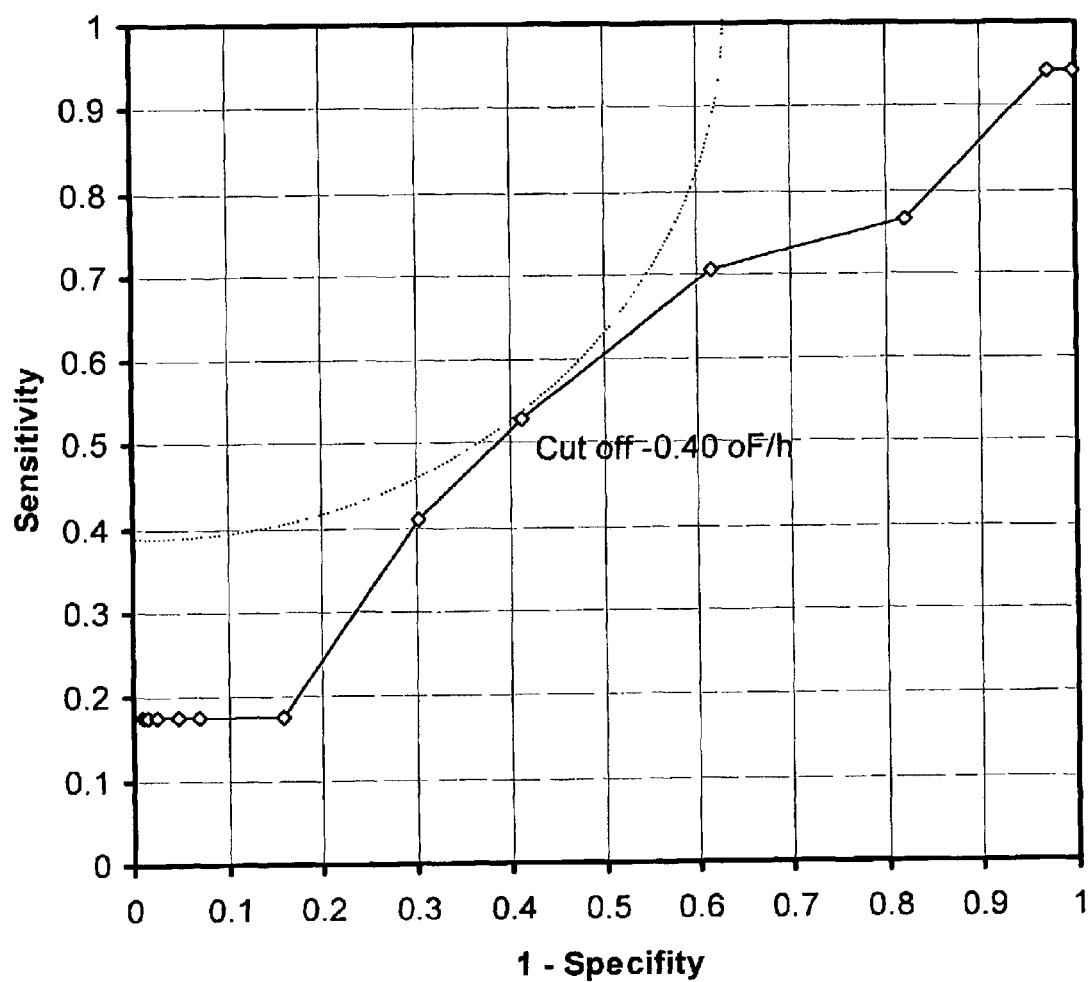
FIG. 3 is a receiver operating characteristic curve for speed of temperature fall as a test for imminent death in CHF patients. The curve plots the sensitivity of rate of fall of temperature on the y-axis vs. 1-specificity of rate of fall of temperature on the x-axis for the data of Table 1.

Using repeated measurements analysis of variance on speed of temperature change, between-subject variations among those 17 (6%) who died of cardiac causes and those who survived was significant (P=0.006), while within-subject variations during the hospital stay were not significant (P>0.3). To determine the sensituvity and specificity of speed of temperature change measurements as a predictor of death, receiver operator curves were implemented, and are shown in FIG. 3.

A rate of temperature fall greater than 0.4° F./h had the optimum sensitivity (53%, CI 95%: 47–59) and specificity (59%, CI 95%: 53–64) to predict death Of the 17 patients who died, 8 had a speed of temperature fall greater than 0.4° F./hr for at least once during their hospitalization, and the time interval between the first time they had it and death had a mean of 112 hrs (CI 95%: 41–183 hrs). ("CI" in the tables is confidence interval; numbers in this textual part are rounded up from those in the tables to two significant figures.)

Figure 4:
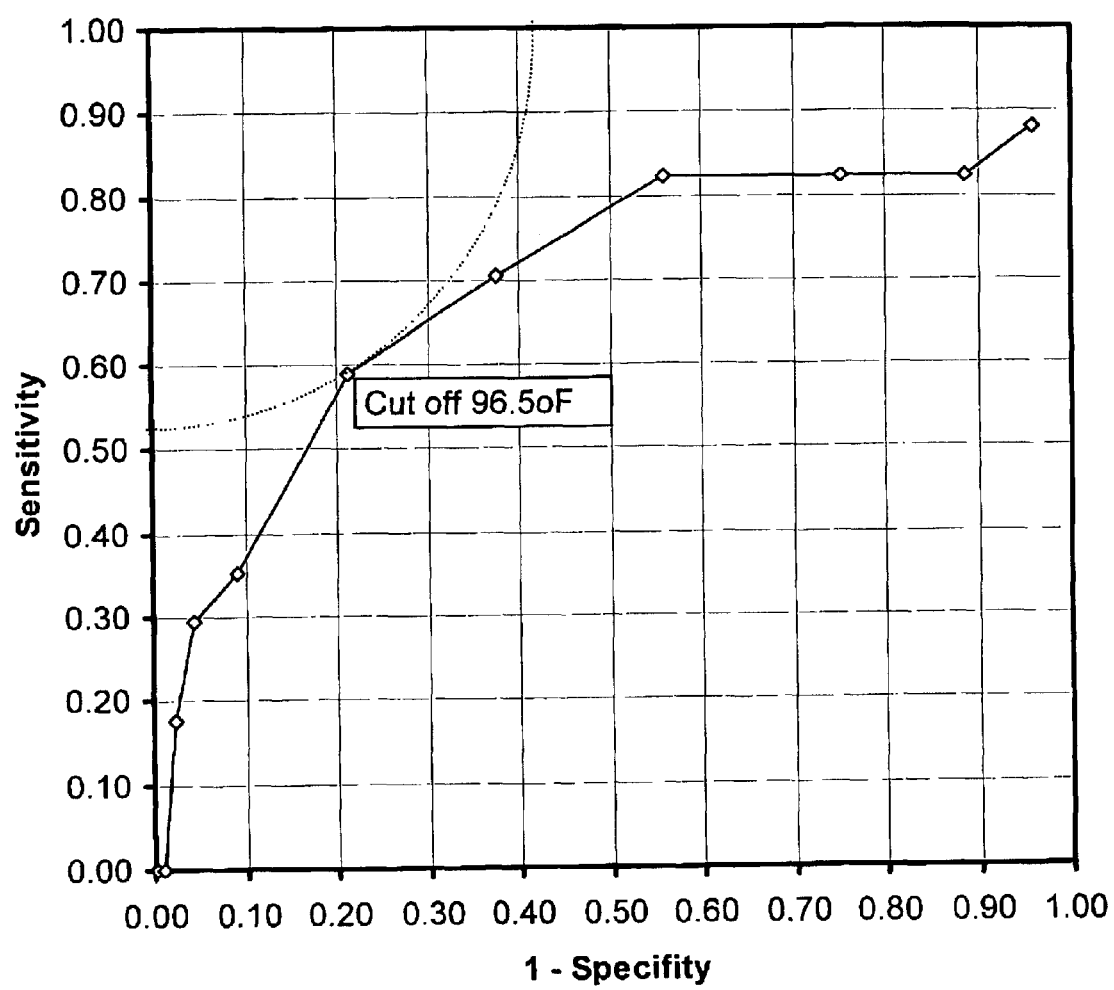
FIG. 4 is a receiver operating characteristic curve for hypothermia on admission as a test for imminent death in CHF patients. The curve plots the sensitivity of temperature at admission on the y-axis vs. 1-specificity of temperature at admission on the x-axis for the data of Table 2.

To determine the sensitivity and specificity of single temperature measurements, receiver operator curves were implemented on temperature measurement at admission. The data based on temperature on admission are set forth in Table 5. The associated receiver operator curve is shown in FIG. 4.

TABLE 5

Sensitivity and specificity for different levels of hypothermia on admission as predictor of death

| Cutoff (° F.) | Specificity | Sensitivity | CI95% Specificity | | CI95% Sensitivity | |
|---|---|---|---|---|---|---|
| 94.00 | 0.9964 | 0.0000 | 0.9894 | 1.0033 | 0.0000 | 0.0000 |
| 94.50 | 0.9891 | 0.0000 | 0.9771 | 1.0010 | 0.0000 | 0.0000 |
| 95.00 | 0.9781 | 0.1765 | 0.9613 | 0.9949 | 0.1327 | 0.2203 |
| 95.50 | 0.9562 | 0.2941 | 0.9327 | 0.9797 | 0.2418 | 0.3465 |
| 96.00 | 0.9088 | 0.3529 | 0.8757 | 0.9418 | 0.2980 | 0.4078 |
| 96.50* | 0.7883 | 0.5882 | 0.7414 | 0.8353 | 0.5317 | 0.6448 |
| 97.00 | 0.6241 | 0.7059 | 0.5684 | 0.6797 | 0.6535 | 0.7582 |

TABLE 5-continued

Sensitivity and specificity for different levels of hypothermia on admission as predictor of death

| Cutoff (° F.) | Specificity | Sensitivity | CI95% | | | |
|---|---|---|---|---|---|---|
| | | | Specificity | | Sensitivity | |
| 97.50 | 0.4416 | 0.8235 | 0.3846 | 0.4987 | 0.7797 | 0.8673 |
| 98.00 | 0.2482 | 0.8235 | 0.1985 | 0.2978 | 0.7797 | 0.8673 |
| 98.50 | 0.1131 | 0.8235 | 0.0767 | 0.1495 | 0.7797 | 0.8673 |
| 99.00 | 0.0401 | 0.8824 | 0.0176 | 0.0627 | 0.8453 | 0.9194 |

(*Bolded figures show optimal sensitivity and specificity.)

Figure 5:
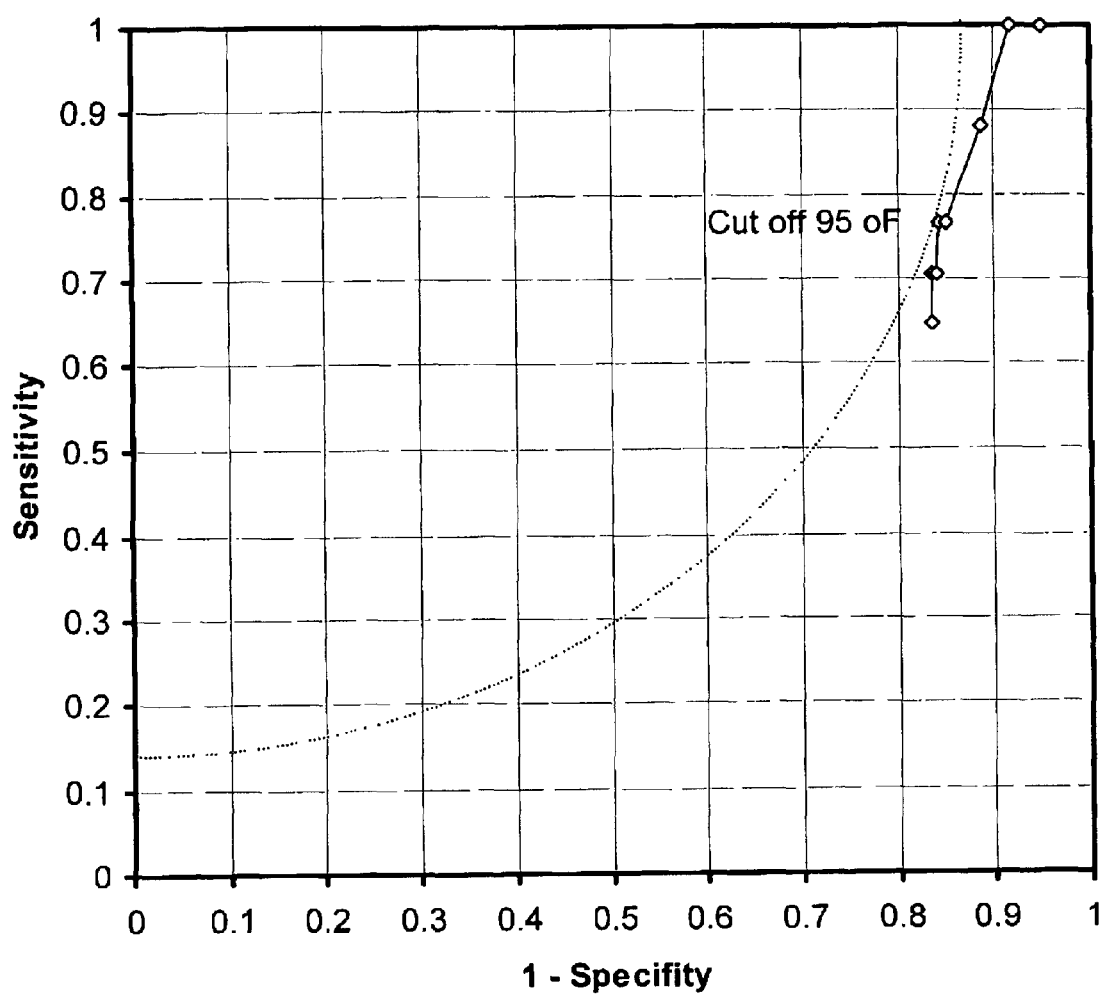
FIG. 5 is a receiver operating characteristic curve for curve for hypothermia as test of imminent death based on repeated temperature measurements during hospitalization. The curve plots the sensitivity of temperature taken on repeated measurements during hospitalization on the y-axis vs. 1-specificity of such temperatures on the x-axis for the data of Table 3.

To further test the sensitivity and specificity of single temperature measurements, receiver operator curves were implemented on all temperatures measured during hospitalizations. The data based on temperature on admission are set forth in Table 6. The associated receiver operator curve is shown in FIG. 5.

TABLE 6

Sensitivity and specificity for different levels of hypothermia as predictor of death on repeated measurements during hospitalization

| Cutoff (° F.) | Specificity | Sensitivity | CI95% | | | |
|---|---|---|---|---|---|---|
| | | | Specificity | | Sensitivity | |
| 91.50 | 0.1642 | 0.6471 | 0.1217 | 0.2068 | 0.5922 | 0.7020 |
| 92.00 | 0.1642 | 0.6471 | 0.1217 | 0.2068 | 0.5922 | 0.7020 |
| 92.50 | 0.1642 | 0.6471 | 0.1217 | 0.2068 | 0.5922 | 0.7020 |
| 93.00 | 0.1642 | 0.7059 | 0.1217 | 0.2068 | 0.6535 | 0.7582 |
| 93.50 | 0.1642 | 0.7059 | 0.1217 | 0.2068 | 0.6535 | 0.7582 |
| 94.00 | 0.1606 | 0.7059 | 0.1184 | 0.2028 | 0.6535 | 0.7582 |
| 94.50 | 0.1606 | 0.7059 | 0.1184 | 0.2028 | 0.6535 | 0.7582 |
| 95.00* | 0.1569 | 0.7647 | 0.1151 | 0.1987 | 0.7160 | 0.8134 |
| 95.50 | 0.1496 | 0.7647 | 0.1086 | 0.1906 | 0.7160 | 0.8134 |
| 96.00 | 0.1131 | 0.8824 | 0.0767 | 0.1495 | 0.8453 | 0.9194 |
| 96.5 | 0.0839 | 1.0000 | 0.0521 | 0.1158 | 1.0000 | 1.0000 |
| 97.00 | 0.0511 | 1.0000 | 0.0258 | 0.0764 | 1.0000 | 1.0000 |

(*Bolded figures show optimal sensitivity and specificity.)

While a temperature less than 96.5° F. on admission had the optimum sensitivity (59%, CI 95%: 53–64) and specificity (79%, CI 95%: 74–83) to predict death, on later measurements, this optimal cutoff point was 95° F., with a sensitivity of 76% (CI 95%: 71–81) and specificity of 16% (CI 95%: 12–20) to predict death.

It has been previously found that in elderly patients, body temperature increases over time during hospitalization. This would explain a greater variation of body temperature among at least a subset of patients, which would change the shape of an ROC curve. In the new ROC curve, the optimal cutoff point correlated to a lower value of temperature, which in this case was more specific and less sensitive.

However, our finding that the speed of temperature change varies insignificantly in individual patients and hence provides a more stable test not been previously reported. More particularly, in continuing this investigation, we have now discovered that rate of fall of temperature of a CHF patient has smaller variations as compared to single temperature measurements at admission or at any time during hospitalization. This was tested using a set of statistical tests that look at variations of rate of fall of temperature and temperature among different patients (between subject variations), and among repeated measures of rate of fall of temperature and temperature in the same patients (inside subject variations). The tests were suggestive of statistically significant variations of temperature among repeated measures of temperature, while the variations of fall of temperature among repeated measures of temperature were insignificant. The same set of tests suggested that variations in fall of temperature among patients who died and survived were different in a statistically significant manner. This indicates that fall of temperature is more stable than temperature as a test for the probability of death in this setting.

In accordance with our invention, the modest sensitivity and specificity of these revealing results (in which temperatures were not taken uniformly either by method or temporally) are improved as a predictive tool, inter alia, by more frequent and uniform measurement, by pre-setting the temperature cut-off point attribute of CHF hypothermia relative to optimum sensitivity and specificity, by referencing determinations of whether cut-off points are attained or crossed to personal baseline set-points, by taking into account circadian and lunar patterns, by adjusting for other internal and external factors, and by combining watch of the cut-off points with information concerning other prognostic factors. If a cut-off point is attained or crossed, an alert is issued. In an aspect of our invention, the alert triggers operation of a device to initiate or adjust medical treatment of the monitored patient directly and immediately.

In an embodiment, the methodology of our invention of monitoring a patient with congestive heart failure, for worsening of such condition, fundamentally comprises (a) presetting a cut-off point of at least one temperature attribute of hypothermia comprising rate of fall of body temperature relative to optimum sensitivity and specificity for such attribute as a congestive heart failure predictor of death of a patient, (b) routinely determining that attribute in the patient, and (c) determining whether that attribute has attained or crossed the cut-off point for it.

As used herein, the tense employed with the words "attain" or "attained" and "cross" or "crossed" is not intended to be limiting to a particular tense stated for grammatical purposes; thus the past tense ("has attained") includes the present tense ("attains") and vice versa.

In the description of our invention, the words "rate of fall of body temperature" or "hypothermic body temperature" are intended to include within their meaning any transformation of those attributes. By "transformation" is meant any pattern, integration, derivations, power and logarithmic transformation of different degree, Fourier analysis, time-series analysis, or any other mathematical treatment founded on a primary measure of temperature or determined fall of temperature, the point being that a programmed digital microcomputer, inside or outside the body, can make the necessary determinations either on data of a primary measurement or calculation or on a transformation of that data, and still be within the ambit of the invention. For example, not by way of limitation, instead of using rate of fall of body temperature over a period of time as a temperature attribute, an integral or summation of temperature fall over a period of time implemented as an accumulator or summing register may be used as a substitute for a determination of a temperature attribute.

As used herein, the "cut-off point" or "cut-off value" of a temperature attribute is the value of the temperature attribute beyond which the test changes from being considered negative to being considered positive.

The "optimum sensitivity and specificity" for a temperature attribute as a congestive heart failure predictor of death of a patient is a particular sensitivity and specificity of that attribute based on data collected in a statistically representative population of subjects having a congestive heart failure, and conveniently is established by generation of a receiver operator characteristic ("ROC") curve, as described above in respect to the discovery investigation. Use of ROC curves to establish an optimal sensitivity or specificity cut-off point is a well known statistical technique. The ROC curve technique in the context of this invention is based on the attributes of hypothermic body temperature and rate of fall of body temperature, and may also be used for amount of body temperature fall in a selected interval, the interval's duration and the frequency of such intervals. As indicated above, the data supporting an ROC curve may be transformed and used in the invention instead of the primary determinants, and such transformations are within the intended scope of language employed describing the temperature attributes comprising hypothermic body temperature, rate of fall of body temperature, amount of body temperature fall in a selected interval, the interval's duration and the frequency of such intervals.

The invention includes setting the cut-off point "relative" to the optimum sensitivity and specificity for the temperature attribute to be measured. By setting the cut-off point "relative" to the optimum is meant to include setting the cut-off point at exactly the optimum value or at a value above or below the optimum value; for example, as a point on an ROC curve, the cut-off point can be set "relative" to optimum by selecting the coordinates point where best sensitivity corresponds to best specificity, or by selecting a coordinate above or below that optimum value on the curve, for either increased specificity and correspondingly less sensitivity or for increased sensitivity and correspondingly less specificity. Thus the cut-off point may be selected by the health care professional above or below the optimum specificity and sensitivity coordinate value for a sensitivity that best suits the patient's individual condition. The relativity to optimum may be a percentage of optimum, a ratio or a fixed value, for example, 10% higher or lower than optimum. As implemented in a mechanism, this can be set, for example, by a dial incrementing or decrementing percentages of the optimum value.

The temperature attribute of hypothermia for which a cut-off point is set relative to optimum sensitivity and specificity for such attribute as a congestive heart failure predictor of death comprises at least rate of fall of temperature. Optionally one or more additional sets of predetermined criteria may be used to alert the patient and/or the patient's health caregiver for proper action or to initiate action of a device that provides medical treatment to the patient. The predetermined criteria are based on research done on patient population cohorts, as exemplified above (e.g., Table 4, FIG. 3). Suitable absolute criteria could include, an as example: (1) a speed of fall greater than –0.4° F./hr; and optionally (2) an interval fall of 1.5° F. or more lasting less than three hours happening more than four times/day; and/or a (3) static temperature less than 95.5° F.

An aspect of our invention is adapting absolute criteria to personalized criteria, that is, relative to the temperature baseline of the patient monitored as contrasted to relative to the temperature baseline of a patient cohort study. Our invention thus includes, in supplemental aspects and embodiments, personalization of a "normal" temperature basis a cohort study, to the CHF patient's own baseline temperature set-point. A patient's set-point or baseline temperature is the temperature which the body attempts to maintain constant. An individual patient's set-point may vary from the average of the general population. The baseline "gold standard" of normal oral temperature in adults is 37° C. (98.6° F.). This standard has been questioned with a "new" mean oral temperature reported as 36.8° C. (98.2° F.) (Mackowiak, P. A., Wasserman, S. S., and Levine, M. M. "A Critical Appraisal of 98.6° F., the Upper Limit of the Normal Body Temperature, and Other Legacies of Carl Reinhold August Wunderlich." *Journal of the American Medical Association*, 1992; 268:1578–1580) ("Our findings conflicted with Wunderlich's in that 36.8° C. (98.2° F.) rather than 37.0° C. (98.6° F.) was the mean oral temperature of our subjects . . . . Thirty-seven degrees centigrade (98.6° F.) should be abandoned as a concept relevant to clinical thermometry . . . "). According to the Mackowiak et al. study, normal is 98.2° F. plus or minus 0.6° F., that is, anything in the range of 97.6° F. (36.4° C.) to 98.8° F. (37.1° C.) should be considered normal. However, studies indicate that some frail elderly patients in nursing homes have a low baseline body temperature, for example, 96° F. (35.6° C.). And since very small temperature changes can be an indicator of imminent death among CHF patients, it is important to determine changes against the patient's personal temperature set-point as contrasted to the average of the general population.

More particularly in reference to personalizing a monitored patient's baseline, our invention comprises a method of determining a selected measure of central tendency and measure of dispersion of the patient's body temperatures to define the patient's own baseline body temperature, thence re-referencing the cut-off point preset from the basis of a "standard" normal body temperature to a basis of the patient's personal baseline body temperature, and, after the re-referencing, determining whether a temperature attribute of hypothermia has attained or crossed the re-referenced cut-off point preset, and if so, outputting an alert. As used herein, "measure of central tendency" means any such measures, including, e.g., mean, median, mode etc., and "measure of dispersion" means any measures of dispersion, including, e.g., range, minimum, maximum, standard deviation, variance, etc., in accordance with the usual terminology; see STATISTICAL METHODS IN MEDICAL RESEARCH, P. Armitage, G. Berry, $2^{nd}$ edition, 1987, pages 26 and 33. In general, in accordance with our invention, an embodiment suitably determines the patient's personal baseline temperature by calculating a measure of central tendency and measure of dispersion, e.g., a mean, median and standard deviation, of the patient's temperatures in measurements taken in many small intervals over a day of 24 hours.

For women before menopause, basal temperature changes on a lunar (28 day) cycle. A woman's basal body temperature (taken at a regular time during the day, say in the morning after a night of sleep), rises slightly at the time of ovulation. The rise in basal body temperature, due to ovarian production of progesterone, persists until the start of menses. The temperature change is minimal, typically 0.5 to 1° F. from baseline temperature.

The patient's baseline temperature is the central tendency temperature within a measure of dispersion over the course of a day, in the case of ovulating women, being slightly higher in most women in the second fortnight of a 28 day month. However, a patient's temperature changes throughout the course of a 24 hour day according to a generally regular rhythm. These circadian rhythms influence body temperature, sleep and wakefulness and a variety of hormonal changes. Body temperature is lowest between about 2 a.m. and 6 a.m., when it starts to rise, just before waking up. A drop in temperature also occurs in most people between 12 p.m. and 4 p.m. In the late afternoon, body temperature can be as much as 2° F. higher than in the morning. In the evening, body temperatures decrease in preparation for sleep. Circadian rhythms are coordinated by small nuclei at the base of the brain, the suprachiasmatic nuclei (SCN). The SCN have connections with other parts of the brain to control the body's temperature, hormone release and other functions. A pathway runs from the eye to the SCN, and light seems to play the largest role in setting the circadian "clock".

A refinement of our invention enhances personalization of the individual patient's temperature basis for a preset cut-off point by determining lunar and circadian changes in temperature of the patient. In general, this is accomplished with respect to temperature as a preset cut-off point by recording the times of a day and days when a temperature is taken and recorded, by cumulatively determining the measure of central tendency and measure of dispersion of these temperatures at those times and dates, and by not recognizing a temperature fall as attaining or crossing a cut-off point preset when the temperature fall is within the measure of dispersion of the patient at that time of the day or on days when basal temperature is higher (for most ovulating women, in the second fortnight of a month). With respect to rate of fall as a cut-off point preset, lunar and circadian personalization is accomplished by recording the times of a day when a temperature is taken and recorded, by cumulatively determining the measure of central tendency and measure of dispersion of temperature rate of fall at those times, and by not recognizing as a attaining or crossing a cut-off point preset a temperature rate of fall when the temperature rate of fall is within the measure of dispersion of the patient at that time of the day. Another way of approaching the same concept is to define the coefficients of the mathematical functions of the circadian and/or lunar rhythms, which is done using modeling mathematics.

Thus, for example, the patient's own baseline temperature variations are suitably determined by measuring the mean, median, standard deviation, and range of temperature readings in a one day period, which in turn would take into consideration the patient's circadian rhythm of temperature, as well as the trend of change over a 28 day period, which in turn would take into consideration the menstrual cyclic changes if present. The patient's normal daily variations of rate of change are suitably determined by calculating mean, median and standard deviation of change per hour measured in a 24 hour period, as well as over a 28 day period.

A patient's environmental status includes outdoor vs. indoor conditions and outside temperature, ambient light, the patient's clothing, use of warming blankets or cooling coverings or other garments. An embodiment of our invention includes determining and making adjustments on the basis of factors external to the patient, including the patient's environmental temperature (suitably detected by external thermosensor) and light (suitably detected by external photosensor), so that the monitor is not falsed by ambient conditions. It is known that with exposure to cold there is a fall in skin temperature and a widening core-skin gradient. In a normal person, the core temperature also may drop slightly and then return to a compensation level at or near baseline as the body compensates for the temperature gradient between surface and environment by routing peripheral blood to the core to conserve heat, by muscle shivering to warm blood in the skeletal musculature, etc. If the patient is in an environment in which he may be chilled, the core temperature might go down for a short period of time and in a small amount as well, but the compensatory process ordinarily will get the core temperature back to a temperature close to normal. The temperature attribute may be adjusted in a direction against the cut-off point (e.g., incrementing the temperature a predetermined amount), or the cut-off point may be adjusted to a position along the ROC curve data set less sensitive relative to optimum sensitivity, to guard against false alarms in this context. Thus in the instance of correcting a temperature reading, it is initially set for the amount of expected change. The amount of expected change is predetermined at the beginning, but using the kind of mathematics that are generally encapsulated as "learning algorithms", a monitoring algorithm is suitably employed to get more and more information about the body's response to the medication or medications and recalculates the expected change.

An especially important purpose of testing for environmental temperatures is its usefulness in serving as an early warning of risk of death or deterioration in CHF and other patients. In accordance with this invention, environmental and core temperatures of a CHF patient are monitored, and if the environmental temperature (air or water) falls sharply, the core temperature of the patient is compared to a data set for core temperatures of a normal person at the environmental temperatures being monitored and if at the same temperatures the core temperature of the patient lags behind the core temperature compensation of a normal person (does not return as fast to the normal compensation temperature) or sustains at a lower temperature than the temperature of a normal person after compensation, then an alert is issued signaling cold stress of a CHF patient.

More particularly, in this latter embodiment, the environmental temperature and core temperatures of the patient are monitored and recorded. Determinations of environmental temperature are periodically made to ascertain whether a steep fall in environmental temperature has occurred. If such a change is determined to have occurred, the patient's core temperature and the patient's change in core temperature over time are compared to a core temperature and a change in core temperature over time of a normal person at environmental temperatures monitored beginning with the temperatures included in the steep fall, and an alert is issued if rise of core temperature of the patient, from a temperature below a baseline temperature of the patient to a temperature at or closer to baseline, lags behind rise of core temperature of the normal person from a temperature below a baseline temperature of the normal person to a temperature at or closer to baseline, or if the core temperature of the patient rises from a temperature below a baseline temperature of the patient to less than a predetermined minimum acceptable rise.

A patient's current physical status includes activity, medications, smoking, alcohol use, and solid and/or fluid intake, and temperature of same. An embodiment of our invention includes determining and making adjustments of periodically determined temperature attributes or their cut-off points on the basis of one or more "internal factors" of the patient, including activity, medications, smoking, alcohol use, and solid and/or fluid intake temperature, so that the monitor is not falsed by internal conditions.

As in the case of environmental temperature, the body temperature attribute may be adjusted in a direction against the cut-off point (e.g., incrementing the temperature a predetermined amount), or the cut-off point may be adjusted to a position along the ROC curve data set less sensitive relative to optimum sensitivity. The amount of expected temperature attribute change is predetermined at the beginning, but a monitoring learning algorithm is suitably employed to get more and more information about the body's temperature attribute response to the medication or medications and recalculate the expected change.

Medications that, if taken, might require correction of the body's temperature attribute being monitored or adjustment of cut-off point sensitivity, include (i) medications affecting the sympathetic nervous system (e.g., beta antagonists such as propranolol and agonists; alpha agonists and antagonists), (ii) aesthetics such as halothane, (iii) GABA agonists such as baclofen and antagonists such as phaclofen, (iv) opioids, (v) estrogen and progesterone, (vi) methamphetamine, (vii) sertonine agonists and antagonists, (viii) angiotensin antagonists, (ix) thyroid medications, (x) nonsteroid anti-inflammatory rigs, and (x) steroids.

Alterative to adjusting for such internal factors, a data set on a cohort study of patients taking the specific medication may be used for setting sensitivity relative to optimum. In such event, no adjustment is required, the ROC curve information natively including the effect of that medication.

Conditions that if present, might require correction of the body's temperature attribute being monitored or adjustment of cut-off point sensitivity, include (i) radiation, (ii) chronic infection, (iii) serum infusion, and (iv) allergic reactions (e.g., hay fever, etc.).

Another internal factor is activity. Activity, as monitored suitably by an accelerometer or a vibration sensor, provides a signal that upon conversion to digital form is usable by a microprocessor, for an adjustment to a temperature attribute or to the sensitivity of detection of that attribute. The same concepts for adjusting a temperature reading or sensitivity of a cut-off point apply as for medications, including use of a learning algorithm to personalize the effect of temperature change from different levels of activity. In general, the same concepts apply to the other mentioned internal factors.

Presetting the specificity and sensitivity and an output route for the warning system customizes the alarming system toward the specific health condition and needs of the patient. The system alarms sooner if the patient is in an otherwise poorer prognostic category, suffers other mental/health disabilities, or is located away from healthcare. This presetting, which is done by the health care professional that oversees the functionality of the device, or which in certain instances may be increased automatically, is based on (1) the patient's other co-morbidities; (2) other prognostic factors; and (3) the time and distance availability of professional and/or nonprofessional healthcare.

A patient's other co-morbidities could include presence of Alzheimer's disease or other dementia, depressive mood, and motor disability.

As respects prognostic factors other than the followed temperature attribute(s), in an aspect of our invention, one or more of them are used to adjust sensitivity of the system. These other prognostic factors can be any one or more of bedside factors such as age, sex, ischemic heart disease, New York Hear Association functional class, S3 gallop, Cheyne-Stokes respiration, apnea/hypopnea index, systolic blood pressure, heart rate at rest, pulse pressure, mean arterial pressure, and cardiac cachexia. Or they can be any one or more of test factors such as chest impedance peak oxygen uptake (dot(V)O2), left and right ventricular ejection function, both respiratory and circulatory response to exercise, cardiac index, left ventricular cavity size, left ventricular stroke work index, right and left ventricular filling pressure, left ventricular filling isovolumic relaxation time, left ventricular systolic pressure, right and left atrial pressure, systemic vascular resistance, calculated wall stress, tricuspid regurgitation, jugular venous pressure, pulmonary capillary wedge pressure, 6-minute walk distance, arterial and venous pH, $pO_2$, $pCO_2$, serum creatinine, serum sodium, plasma norepinephrine, plasma neurotensin, plasma renin activity, plasma arginine vasopressin, plasma atrial and brain natriuretic peptides, plasma endothelin-1, plasma interleukin-6, plasma tumor necrosis-alpha, serum sodium, serum potassium, total potassium stores, serum magnesium, lymphocyte count, frequent ventricular extrasystoles, ventricular tachycardia, left bundle-branch blockage, right bundle-branch blockage, atrial fibrillation or flutter, T-wave alternans, QT prolongation, and QT dispersion.

Most of the foregoing prognostic factors mentioned cannot be measured continuously by a mechanism wearable by an ambulatory patient or implantable inside the body and would be limited to use in a hospital environment. Those that can be measured continuously by a mechanism wearable by or implantable in an ambulatory patient include QRS duration, QT interval changes, heart rate at rest, systolic blood pressure, pulse pressure, mean arterial pressure, right atrial pressure, right ventricular filling pressure, and pulmonary capillary wedge pressure. QT interval changes, QT interval, venous oxygen saturation, venous pH, right ventricle pressure and speed of change of pressure, and respiratory rate all are suitably measured continuously by an implanted sensor (an implantable sensor, is, however, not appropriate for patients with severe lung disease). Means that provide at least some of the above mentioned information to a processing and alarming unit in accordance with this invention include an implantable chest impedometer, implantable devices known to those of ordinary skill in the art that monitor electrical activity of the heart, and implantable devices known to those of ordinary skill in the art that monitor the patient's respiration.

If the bedside risk factors are high, e.g., an age equal or greater than 70, presence of ischemic heart disease, and a NYHA classification of 3 or higher, the health care professional can increase the preset sensitivity from the optimal point by, for example, 5%. Or if any one or more or a complex of the above listed measured testing factors is known from in-hospital auxiliary monitors or testing, the health care professional can increase sensitivity of a monitor embodiment of this invention relative to optimum for the temperature attribute being determined by a selected percentage. The degree of increase of sensitivity will be a professional judgment.

In accordance with this invention, an implanted device may provide, to analyzer of this invention, information concerning any one or more of the factors listed above that can be continuously monitored in an ambulatory patient, and the information so provided can be used to determine an adjustment and to automatically adjust a temperature attribute or the sensitivity of an attribute being determined, as described above in connection with adjusting for internal and/or external factors.

A factor relevant to a health care provider's setting sensitivity "relative" to optimum is availability of immediate care by a healthcare provider. If care is available within seconds as in intensive care, sensitivity can be decreased, if appropriate in the context of other prognostic factors. Immediacy of care availability to a patient ranges outwardly in time and distance from seconds in intensive care, to minutes in-patient ward care, to within up to about 24 hours for an out-patient living near the hospital (e.g., a person living with healthy others close to medical centers in large cities), to more than about 24 hours delay for a patient living some long distance away from the hospital (e.g., a person living alone in small cities). Considering the "time and distance" factor, the health care professional will pre-set the temperature attribute cut-off point, relative to optimum sensitivity and specificity for that temperature attribute, in a range from a larger decrease, for care immediately available as intensive care, to a larger increase, for care available with more than 24 hours delay. Thus, in an example, the availability of professional and/or nonprofessional healthcare suitably may be classified in four categories; category 1, for example, could have a present sensitivity 10% lower than optimal, and category 4, for example, could have a preset sensitivity 10% higher than optimal.

A feature of the invention is output of an alert if a temperature has attained or crossed the cut-off point or if core and peripheral temperatures of a patient are both moving in the direction of a cut-off point, or if a patient is determined to have an inadequate response to exposure to a cold environment. The alert may be output to the patient and to the health care provider, by wired or wireless means, locally or telecommunicated, or to a device for starting or adjusting medical treatment on a patient. The alarming process may have routes of output to the patient himself and to his or her health caregivers. The alarming for the patient suitably includes one or more of a sound signal, a voice signal (robotic message, prerecorded human voice, a vibratory alarm, or a visual alarm (blinking light). The alarming for the health caregiver suitably includes one or more of an automated call made to one or more of a set of predefined phone numbers and wired or wireless communication with a closely located monitoring center. If a co-morbidity is present and is considered in setting the cut-off point relative to optimum, and if the co-morbidity is any of Alzheimer's disease or other dementia, depressive mood, and motor disability, the output of the alert is directed at minimum to a healthcare provider, since the patient is unlikely to be able to help themselves.

In an embodiment of this invention, a monitoring device of this invention is in communication with and controls the operation of another device that is used to therapeutically treat the patient. Such a controlled device suitably is a medication release device, such as a controlled implantable substance release device or an external controlled drug infusion device; a device used to support the pump function of the heart such as a ventricular assist device; a device that is used to control the rhythm of heart such as a pacemaker or defibrillator; or a warming device.

Body sites to measure body temperature can be characterized as "core" or "peripheral" sites, meaning deep inside the body or near the surface, but even sites classified in that manner do not necessarily behave in the same way. As used herein, "body temperature" comprises a core or peripheral (skin or cutaneous) temperature of the body. One requirement of a core temperature measurement site is that it has to be near an artery, since the blood is the main vehicle for heat loss or heat conservation. A tympanic thermometer, which uses an infrared thermometer to sense infrared energy coming from the tympanic membrane and surrounding ear canal (aural temperature), provides a good measure of arterial blood temperature near the brain. Rectal temperature is usually a few tenths of a degree higher than arterial blood temperature. This method of measurement can be affected by cool blood returning from the lower extremities, insulation by feces and heat producing organisms in the bowel. Bladder temperature compares favorably to temperature measured with rectal probes. Oral cavity temperatures, used for convenience, are less reliable as a core temperature than aural temperatures and tend to be 0.3–0.65° C. (0.54–1.17° F.) below rectal temperature. Axillary (armpit) temperatures are peripheral or cutaneous measurements used for convenience but are more inaccurate than oral temperatures for measurement of core temperature; they are generally 0.5° C. (0.9° F.) below oral temperatures and 1° C. (1.8° F.) below rectal temperatures. Cutaneous temperatures are useful for measuring peripheral temperatures and can be used to measure general temperature trends. Other places of measuring core temperature are used in surgery. Tympanic membrane temperatures ordinarily taken using a contact probe closely approximate brain temperatures and are a highly reliable method of measuring core temperatures. Other places of core measurement include the pulmonary artery, the esophagus, and the nasopharynx. Rectal and bladder temperatures may also be tracked in surgery.

Mounts for internal placement that may be used to obtain core temperatures include an indwelling medical device such as an implanted capsule, a needle, tube, catheter, line, pacemaker, implanted pump and implanted defibrillator. Such tube may be from the group consisting of a nasogastric tube, Dubbhoff tube, endotracheal tube, rectal tube, T-tubes, drain, and nasal probe. The catheter may be a urinary catheter, pulmonary artery catheter, triple-lumen catheter, dialysis catheter, Hickman catheter, and infusion catheter.

Mounts for external placement that may be used include, without limitation, an umbilical sensor, skin electrode, tympanic ear sensor, pulse oximeter, casts, and adhesive based mounts.

Temperature sensors may be any temperature sensor known that is practically applicable, and include thermocouples, resistance temperature detectors or thermistors, thermosensitive chromophores, thermosensitive liquid crystals, infrared detectors and ultrasound detectors.

Alerts may be output by a text display, sound, shock, change in color or shape, warmth, or vibration, or as mentioned above, to a medical device.

In an embodiment, in accordance with our invention, there is provided apparatus for monitoring and warning of worsening of condition of congestive heart failure in a patient, comprising a temperature sensor for sensing body temperatures of a patient and outputting signals representative of the sensed temperatures, a mount of the temperature sensor for indwelling or external placement on the patient, and an analyzer including a digital signal processor, program memory and data memory. The program memory contains a program data set having a cut-off point for at least one temperature attribute of hypothermia as a congestive heart failure predictor of death of a patient. An algorithm in the program memory instructs the processor to perform functions including periodically writing and reading data based on the temperature representation signals respectively to and from the data memory, and to periodically compare data from data memory with data in the program data set to determine whether a temperature attribute has attained or crossed the cut-off point, and if so, to output a signal indicative of cut-off point attainment or crossover. An alarm receives the output signal from the processor and expresses an alert.

Figure 6:
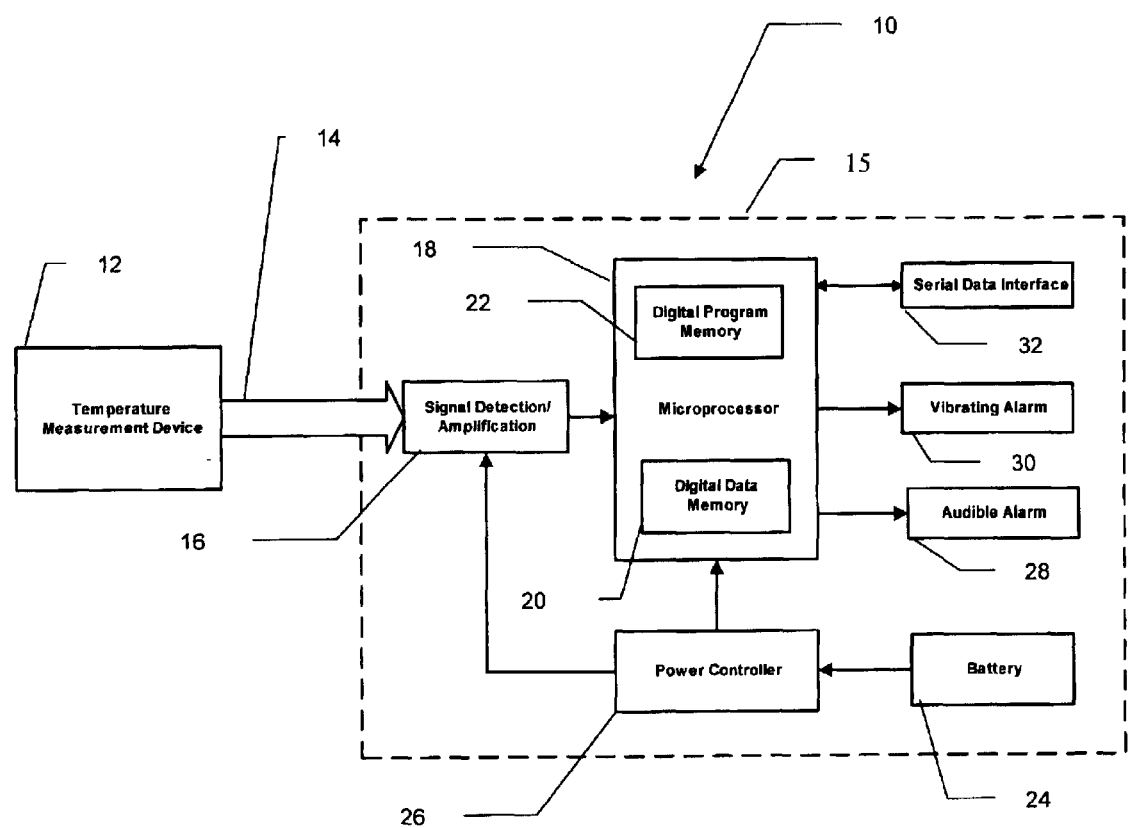
FIG. 6 is a block diagram illustrating apparatus for sensing, monitoring, determining and signaling a condition of CHF hypothermia.

Referring to FIG. 6, reference numeral 10 indicates an apparatus for monitoring and warning of worsening of condition of congestive heart failure in a patient. Apparatus 10 comprises two parts: one portion is an analyzer with basic processor assembly 18, digital program memory 22 (e.g. EPROM), digital data memory (RAM) 20, signal detector/conditioner and amplifier transducer 16, power supply 24 and power controller 26, the analyzer outputting to alarms 28, 30, all contained in a housing 15 with a connection to the outside world via an RS-232 link 32. The other part is the sensor 12 and its signal path 14. Housing 15 suitably is carried as a beltpack and is adaptable so that one sensor could be used for surface temperature detection (cutaneous), as described below, while another type is used for internal (core) measurements. The output of each of these systems is an analog signal in a range that would be fed into a transducer 16 inclusive of an A-D converter in beltpack 15. Suitably processor 18 would signal when to energize the sensor part of the circuit for power saving considerations.

More particularly, temperature sensor 12 senses body temperatures of a patient. Temperature sensor 12 suitably is an infrared thermometer for sensing radiation from perfusion of the tympanic membrane, similar to the off-the-shelf, in-the-ear, handheld thermometers used for infants. The electronics interpreting the sensed radiation are in the thermometer in these available devices. Sensor 12 is be placed in the patient's ear, via an ear clip mount 13, with communication link wires 14 running to beltpack 15. Alternatively, the same infrared thermometer may be used but with the temperature detector electronics located on beltpack 15, and with the communications link to beltpack 15 being a fiber optic cable 14 going into the ear for transmitting the infrared signal. This lightens the ear piece mount 13, and allows sensor 12 to be incorporated into a hearing aid for the mount 13. Fiber optic cable 14 is non-metallic and is not susceptible to outside influences or a shock hazard.

Alternatively, sensor 12 may be a temperature controlled oscillator in a capsule 13 embedded in the skin such as skin near the waist. Capsule 13 sends the temperature signal to beltpack 15 by telemetry. Beltpack 15 provides the power for interrogate and read telemetry signal transmission to and from capsule 13, similar to radio frequency transducers for use in EZ Tag lane systems now in use. The communications link 14 is a wireless transmission. This has advantages in that the sensor is not a disposable and is insulated from and uninfluenced by the environment. Plus, there are no connections to be made or broken when changing a disposable, and the sensor is unaffected by bathing, moisture, etc.

The infrared and encapsulated radio frequency oscillator sensors sense core temperatures. Alternatively, or in addition, surface temperatures may be detected. Suitably, in such instance, sensor 12 may be a strip of resistance temperature detectors (RTD's) embedded in a material 13 adherable to the skin, such as in the armpit or in several different locations for temperature pattern detecting. An electrical cable 14 transmits signals from the RTD sensors 12 to beltpack 15. This has advantages in allowing very light weight, relatively economical sensors located in a less cumbersome area of the body, but there are still electrical wires and connections to contend with. Alternatively, sensors 12 may be a cholesteric system embedded in a material 13 adherable to the skin, such as in the armpit or in several different locations for temperature pattern detecting, and communications link 14 may be a fiber optic cable from the sensing point to beltpack 15. This has advantages in that a fiber optic cable 14 is non-metallic and is not susceptible to outside influences or a shock hazard, and the sensors 12 would be less susceptible to water.

The signals from sensor 12 to beltpack 15 are received, conditioned and amplified in transducer 16. Where sensor 12 is an infrared sensor connected by electric cable to analyzer 15, transducer 16 comprises an electronic amplifier. Where sensor 12 is an infrared sensor connected by fiber optic cable to analyzer 15, transducer 16 comprises an infrared detector. Where sensor 12 is a temperature controlled crystal oscillator connected by telemetry to analyzer 15, transducer 16 comprises a radio frequency transceiver. Where sensor 12 is a resistance temperature device connected by electric cable to analyzer 15, transducer 16 comprises a bridge amplifier. Where sensor 12 is a cholesteric crystal connected by fiber optic cable to analyzer 15, transducer 16 comprises an optical color illuminator for illuminating the crystal and a detector for detecting spectral changes in the crystal as a result of change of temperature of the crystal and for converting the detected changes to a digital signal.

Transducer 16 is powered by a power supply (battery) 24 controlled by a power controller 26 managed by analyzer microprocessor 18, which is also powered by power supply 24. The output of transducer 16 is passed to microprocessor 18 that receives instructions from analyzer digital program memory 22 and dispatches and records data and calculation determinations to analyzer digital data memory 20 from which it also extracts data for calculations or output. Under the direction of algorithms in the digital program memory, analyzer microprocessor 18 issues alarms suitably audible 28 or vibrating 30 to the patient or suitably by interface 32, to a device. Serial data device 32 also allows connection to analyzer programmable memory 22 for reprogramming the instruction algorithms of program memory, including setting sensitivities relative to optimum as has been described above. In addition, it permits access and offloading of temperature data recorded and held in data memory 20. The audible alarm 28 has a volume control and suitably may have an ambient noise detector to set the volume automatically.

Beltpack 15 is low powered so that it may operate with batteries and without too much weight for the patient. Apparatus 10 provides 24 hour monitoring; to accomplish this beltpack 15 has an interchangeable battery pack for charging separate from the unit. Both sensor 12 and beltpack 15 are suitably water resistant, including connections and battery, but need not be submersible. Beltpack 15 suitably detects loss-of-signal from any temperature detector, has a battery checking function or alert, with sufficient time to get to a charger or replacement battery pack, has an On-Off switch with a self-test upon start up and an alert when the unit is switched off (the On-Off switch may also serve as a reset switch), and withstands normal drop testing and mechanical shock criteria. The circuitry of beltpack 15 is not falsed by normal, household electromagnetic inductance, such as microwave ovens or large screen TVs. Suitably and optionally a bypass switch bypasses detection during hot showers and cold weather.

In an embodiment of the invention, the data that is periodically written to and read from the data memory includes body temperature, and the cut-off point in the program memory set includes a body temperature cut-off point. In an embodiment of the invention, the data that is periodically written to and read from the data memory includes a calculated rate of fall of body temperature, and the cut-off point in the program memory set includes a rate of fall of body temperature cut-off point. In an embodiment of the invention, the algorithm includes instructions for instructing the processor to determine a selected measure of central tendency and measure of dispersion of patient body temperature to define the patient's own baseline body temperature, and to re-reference the cut-off point to the baseline body temperature.

In an embodiment of the invention, the program data set is further characterized as comprising a range of sensitivity and specificity pairs, each pair having a cut-off point for at least one temperature attribute of hypothermia as a congestive heart failure predictor of death of a patient, the range including a sensitivity and a specificity pair for an optimal cut-off point of the temperature attribute, and the apparatus further comprises an adjuster communicable with the analyzer for pre-setting a cut-off point relative to optimum sensitivity and specificity for that temperature attribute in the program data set.

In an embodiment of the invention, the program data set includes data comprising a predefined limit pattern of maximum amount of body temperature fall in a selected interval, the interval's duration and the frequency of such intervals, and the algorithm includes instructions for instructing the processor (i) to periodically determine the maximum amount of body temperature fall in a selected interval, the interval's duration, and the frequency of such intervals, as a set, (ii) to determine whether the set exceeds the limit pattern in the program data set, and if so, (iii) to output a signal indicative of attainment or crossover of the limit pattern.

Figure 7:
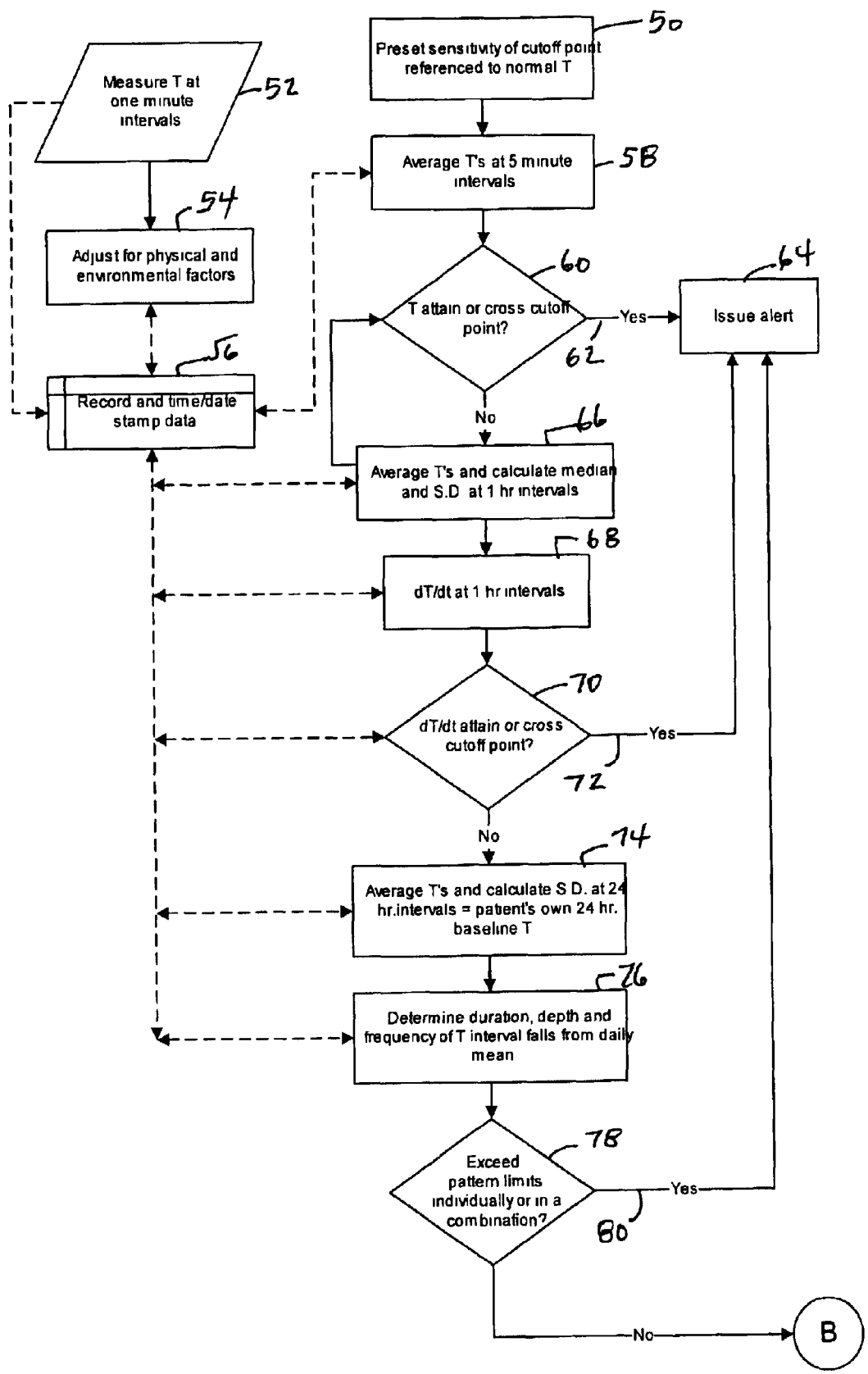
FIG. 7 is a flow chart schematically showing a sequence of operations performable by an algorithm in apparatus of this invention.
Figure 8:
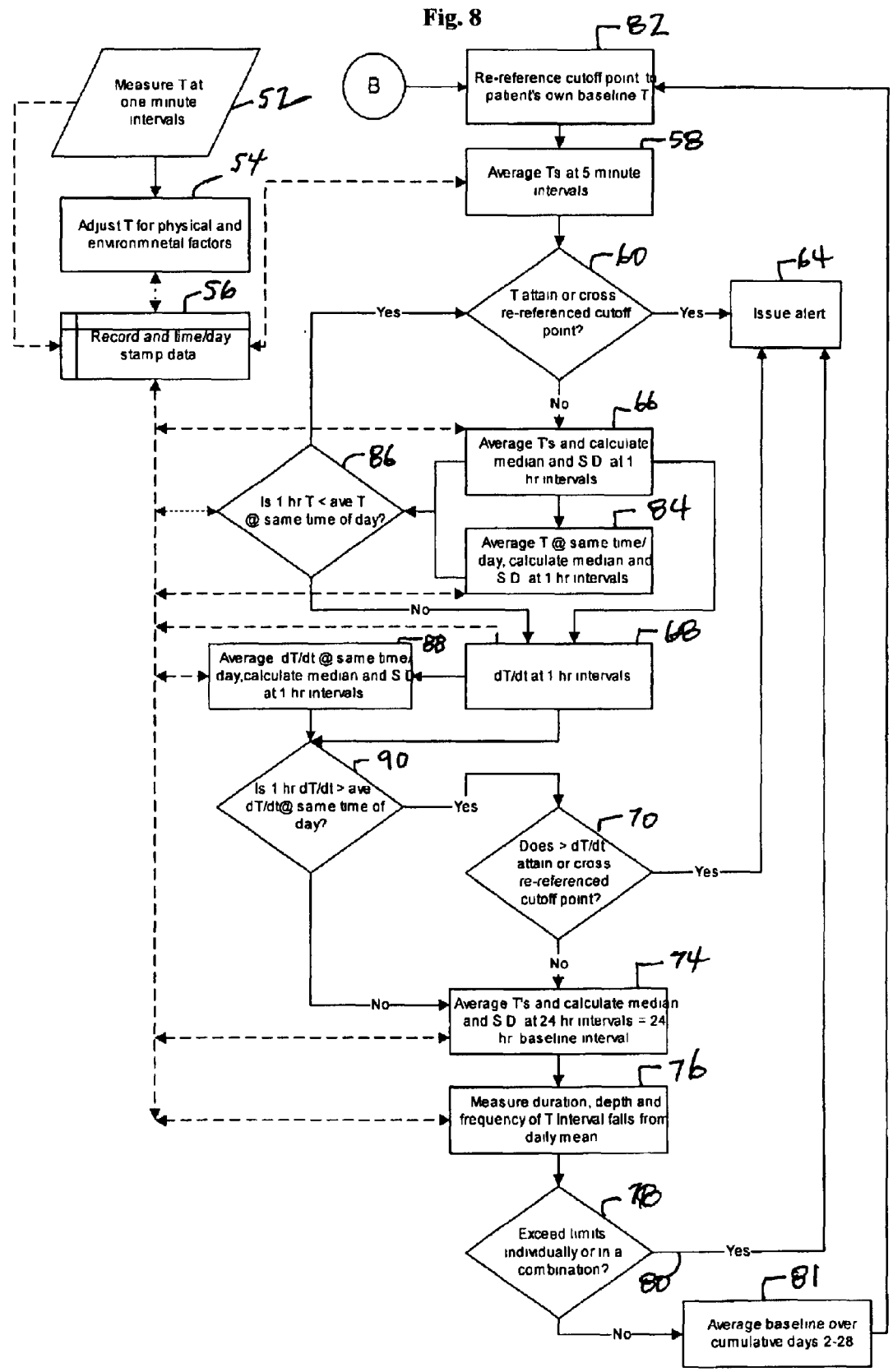
FIG. 8 is a continuation of the chart of FIG. 7.

Referring to FIGS. 7 and 8, a flow path depicts operations that may be conducted in accordance with this invention. Dashed lines indicate read or write operations to data recorder 20.

Suitably by means of RS-232 link 32, a cutoff point of at least one temperature attribute of hypothermia comprising rate of fall of body temperature relative to optimum sensitivity and specificity for such attribute is preset, as at 50, to program memory 22. At one minute intervals, as indicated at 52, microprocessor 18 interrogates sensor 12 and receives signals representative of a sensed temperature of the patient which it writes to data memory 20. The sensed temperature is adjusted at 54 by analyzer 18 for physical and environmental factors, and is recorded at 56 in digital data memory 20 with a time and date stamp.

At five minute intervals, as indicated at 58, microprocessor 18 accesses memory 20 to get the last five temperature records and averages those temperatures. Microprocessor 18 writes that determination to data memory 20 and at 60 compares the determined average temperature to the preset cutoff point from program data 18 to determine whether the 5 minute average temperature has attained or has crossed the preset cut-off point. If the determination is positive, microprocessor 18 outputs a signal as indicated at 62 to issue an alert, at 64, to an alarm, 28 or 32 or both 28 and 32. If the determination is negative, analyzer microprocessor 18 continues the operations at 52, 54 56, every minute, and at 58 and 60, every five minutes.

At 66, microprocessor 18 accesses data memory 20 and retrieves the last 12 five minute average temperatures, averages them, and calculates a measure of central tendency (in this example, mean and median) and a measure of dispersion (in this example, standard deviation) of the sensed temperatures and writes that determined information to data memory 20. At 68, microprocessor 18 determines the rate of any change of temperature over the same one hour interval (dT/dt). At 70, microprocessor 18 compares the determined rate of any change of temperature over the same one hour interval to a preset cutoff point for rate of fall of body temperature relative to optimum sensitivity and specificity for such attribute from program data 18, to determine whether the determined rate of any change of temperature over the one hour interval has attained or has crossed that preset cut-off point. If it has, microprocessor 18 outputs a signal as indicated at 72 to issue an alert at 64 to an alarm, 28 or 32 or both 28 and 32. If the dT/dt determination is negative, analyzer microprocessor 18 continues the operations at 52, 54 56, every minute, and at 58 and 60, every five minutes, and at 66, 68, and 70 every hour.

At 74, microprocessor 18 accesses data memory 20 and retrieves the last 24 one hour average temperatures, averages them, and calculates a measure of central tendency and measure of dispersion of the sensed temperatures and writes that determined information to data memory 20. This information is the patient's personal baseline temperature measure of central tendency and measure of dispersion.

At 76, microprocessor 18 determines the duration, depth and frequency of temperature interval falls from the daily measure of central tendency determined at 74 and at 78 compares the results of those determinations to cut-off points for such information preset in program data 22, to determine whether the duration, depth and frequency of temperature interval falls from the daily measure of central tendency determined at 74 have attained or crossed the preset cut-off points for those variables. If it has, microprocessor 18 outputs a signal as indicated at 80 to issue an alert at 64 to an alarm, 28 or 32 or both 28 and 32.

If not, analyzer microprocessor 18 accesses the 24-hour measure of central tendency and measure of dispersion information from data memory 20 and (referring now to FIG. 8, tracing continuation marker "B" to 82) re-references the sensitivity and specificity data points in program memory 22 by the amount of the differences between the patient's own baseline numbers and a "normal" temperature measure of central tendency and variation.

Microprocessor 18 then continues the operations at 52, 54 56, every minute, at 58 and 60, every five minutes, and at 66 and 68 every hour using the re-referenced baseline numbers, except that having now accumulated temperatures at stamped times of day for a day (24 hours) plus one hour, microprocessor 18 not only at 66 determines the measure of central tendency of temperature value over the hour and calculates the measure of dispersion of the temperature values for the latest hour but also accesses from data storage 20 the cumulative measure of central tendency of temperature value and cumulative measure of dispersion of the temperature value for that same hour of the day (in the initial instance cumulative for only one day) and at 84 calculates a cumulative measure of central tendency of temperature value and cumulative measure of dispersion of the temperature value at that particular hour of the day. At 86, microprocessor 18 determines whether the one hour median and standard deviation temperature calculated at 66 is less than the cumulative median and standard deviation temperature at that time of the day. If it is, microprocessor 18 uses the one hour result from 66 in operation 60, as in FIG. 7. If at 86 the one hour median and standard deviation temperature calculated at 66 is not less than the cumulative median and standard deviation temperature at that time of the day, microprocessor 18 at 68 uses the results at 66 for determination of rate of any change of temperature over the last one hour interval.

At 88, microprocessor 18 takes the result at 68 and accessing from data storage 20 the cumulative measure of central tendency of temperature value, median and standard deviation temperatures of rate of temperature change for that same hour of the day, calculates an updated cumulative measure of central tendency of temperature value, median and standard deviation temperature at that particular hour of the day. At 90 microprocessor 18 compares the determined rate of any change of temperature over the last one hour interval from 68 to the cumulative median and standard deviation temperature at that same hour for the prior day from 88 and determines whether the rate of any change of temperature for that one hour interval at that time of day is larger than expected at that particular hour of the day based on the cumulative median and standard deviation temperature for that particular hour. If it is, microprocessor 18 uses the one hour rate of temperature change result from 68 in operation 70, as in FIG. 7. If at 90 the one hour rate of temperature change calculated at 68 is not less than the cumulative median and standard deviation temperature at that time of the day, microprocessor 18 at 74 uses the results from 70, as previous explained, to calculate a cumulative 48 hour median and standard deviation of the sensed temperatures, writing the data to data memory 20 to update the patient's personal baseline temperature measure of central tendency and measure of dispersion over a longer period. As in FIG. 7, operations at 76 and 78 are then carried out, and if the result is negative, the revised baseline data at 81 from 76 is used to re-reference the cut-off points at 82.

The operations in FIG. 8 are continuously repeated day to day, each day building more data for cumulatively refining the patient's dynamic data, with cumulatively refined circadian and lunar data making the operations at 86 and 90 increasingly sensitive.

In an embodiment of the invention, a mount for external placement on the patient is provided for an environmental factor sensor that detects an environmental factor affecting patient temperature and outputs signals representative of the sensed environmental factor, and the algorithm includes instructions for receiving such signals representative of the sensed environmental factor and adjusting the signals representative of body temperature of the patient to correct for variation caused by the environmental factor.

Figure 9:
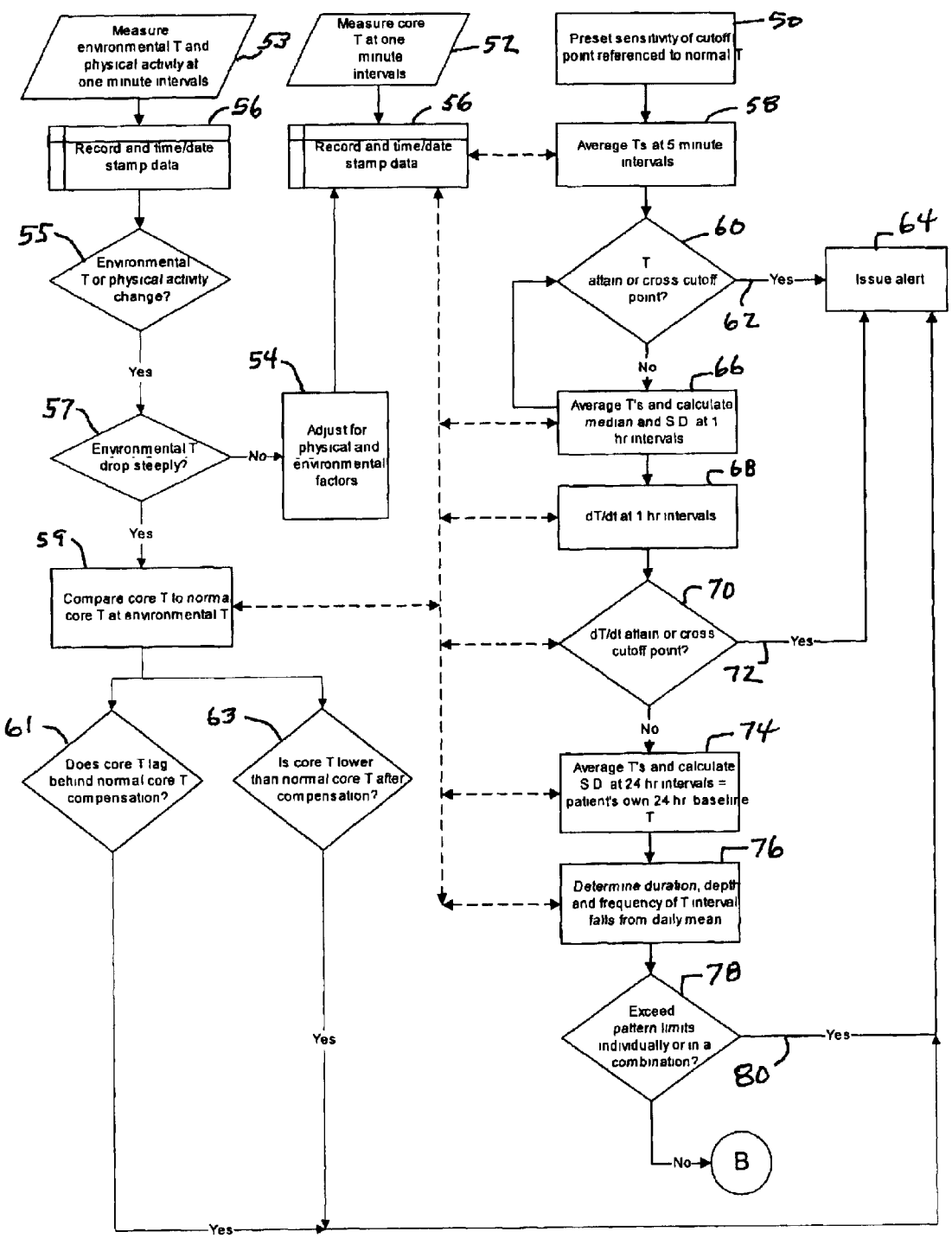
FIG. 9 is a flow chart schematically showing a sequence of operations performable by an algorithm in apparatus of this invention.

Referring to FIG. 9, microprocessor 18 under instructions from the algorithm interrogates at one minute intervals a thermosensor and an accelerometer as at 53 to obtain information about the environmental temperature and the extent of activity of the patient and writes that information to data memory 20 with a time/date stamp as at 56. At 55, microprocessor determines whether there has been a change in the environmental temperature form prior measurements, and also determines whether there is a change in the level of activity of the patient from prior measurements, and if so, at 57 determines whether there has been a steep drop in temperature, indicating exposure to a cold environment (air or water). If not, microprocessor 18 adjusts the measured temperature from 52 for environmental temperature and physical activity. If yes, microprocessor 18 at 59 compares the patient's core temperature and the patient's change in core temperature over time from 56 to data in program memory 22 for a core temperature and a change in core temperature over time of a normal person at the environmental temperatures monitored beginning with the temperatures included in the steep fall, and determines at 61 from data in data memory 20 whether rise of core temperature of the patient from a temperature below a baseline temperature of the patient (baseline temperature as preset as at 50 or re-referenced as at 82) to a temperature at or closer to baseline lags behind rise of core temperature of the normal person from a temperature below a baseline temperature of the normal person to a temperature at or closer to baseline. If not, no action is taken. If there is a lag (program memory 22 containing the definition of lag for the context of the measurement), an alert signal is issued at 64. Microprocessor 18 also determines at 63 whether the core temperature of the patient has risen from a temperature below a baseline temperature of the patient to less than a predetermined minimum acceptable rise. If not, no action is taken. If the rise is less than a predetermined minimum acceptable rise, the patient's cardiovascular system is unable to meet the stress challenge of the cold environment, and an alert is issued at 64.

Figure 10:
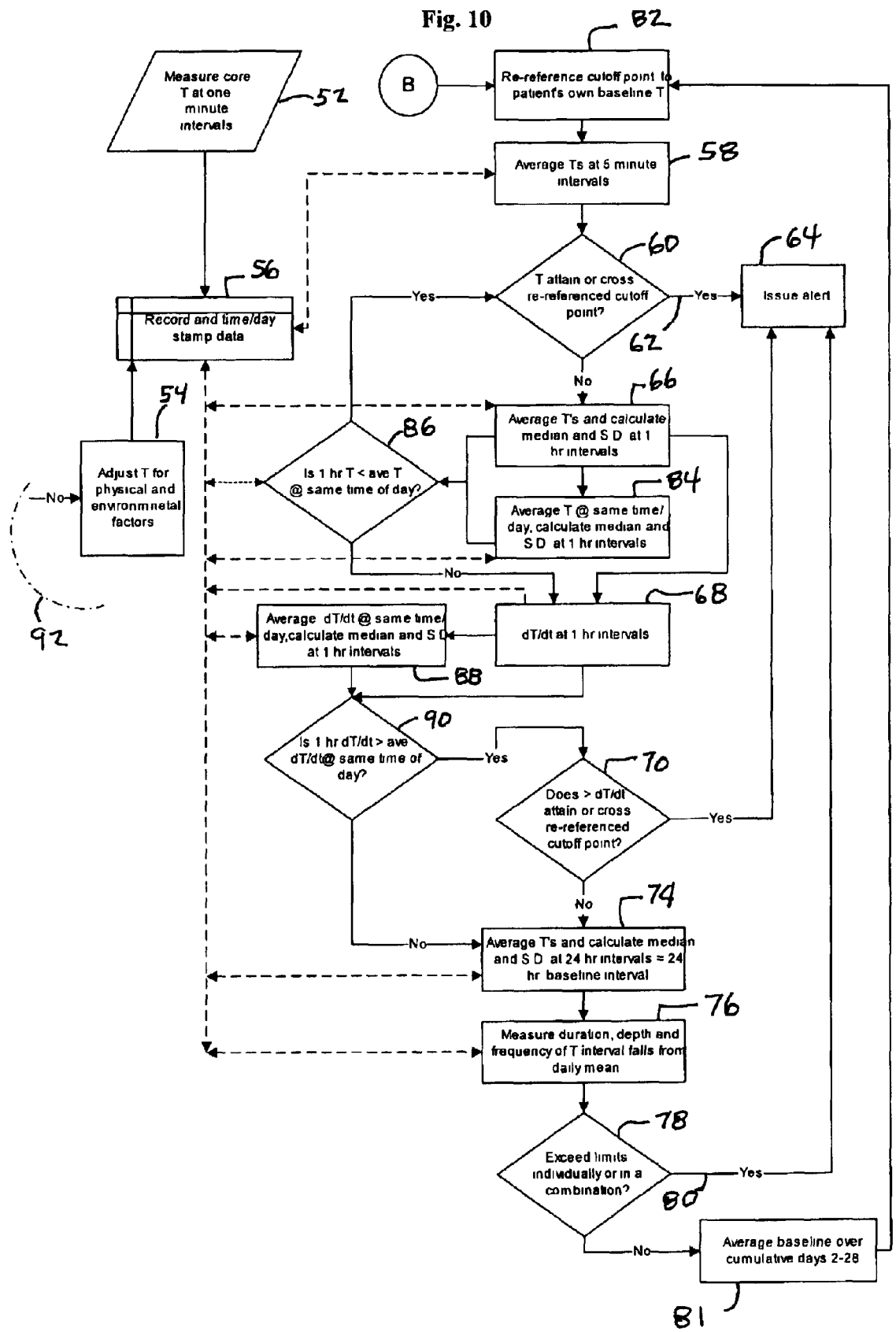
FIG. 10 is a continuation of the chart of FIG. 9.

FIG. 10 indicates conduct of the same operations as described in connection with FIG. 8, with the same ongoing environmental checks as described in connection with FIG. 9, to be understood ongoing (as in FIG. 9) to the left of break line 92.

Figure 11:
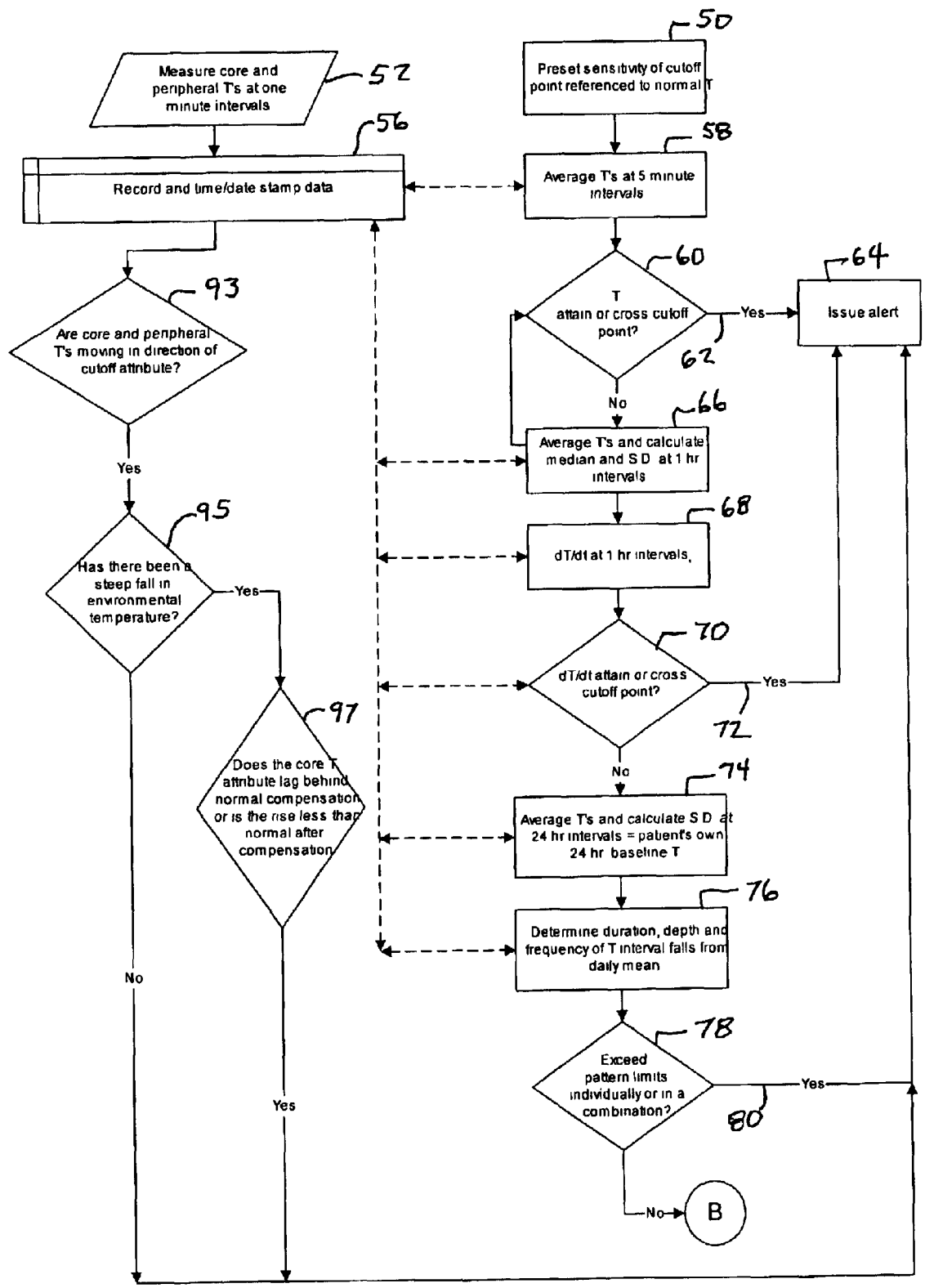
FIG. 11 is a flow chart schematically showing a sequence of operations performable by an algorithm in apparatus of this invention.
Figure 12:
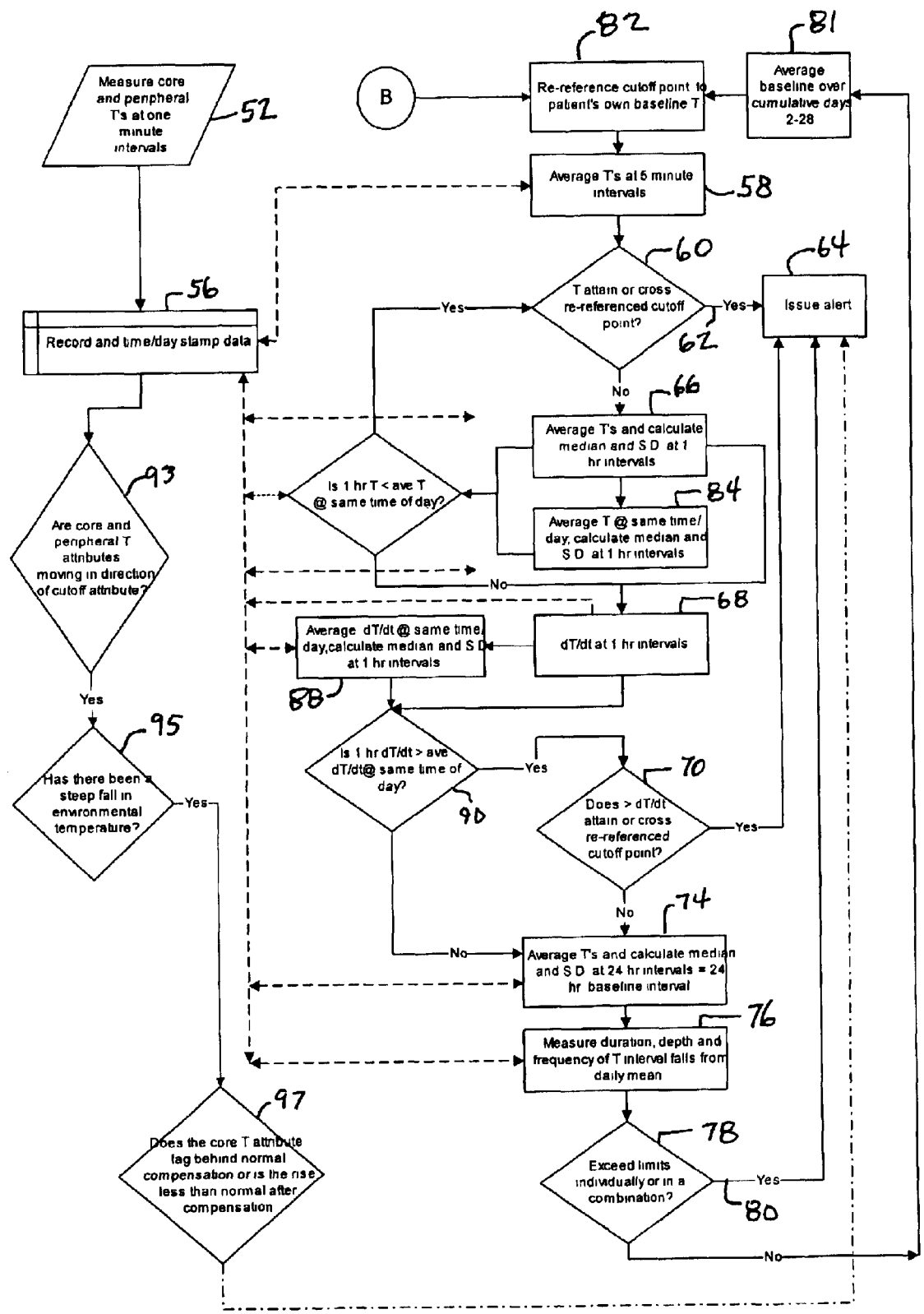
FIG. 12 is a continuation of the chart of FIG. 11.
Figure 13:
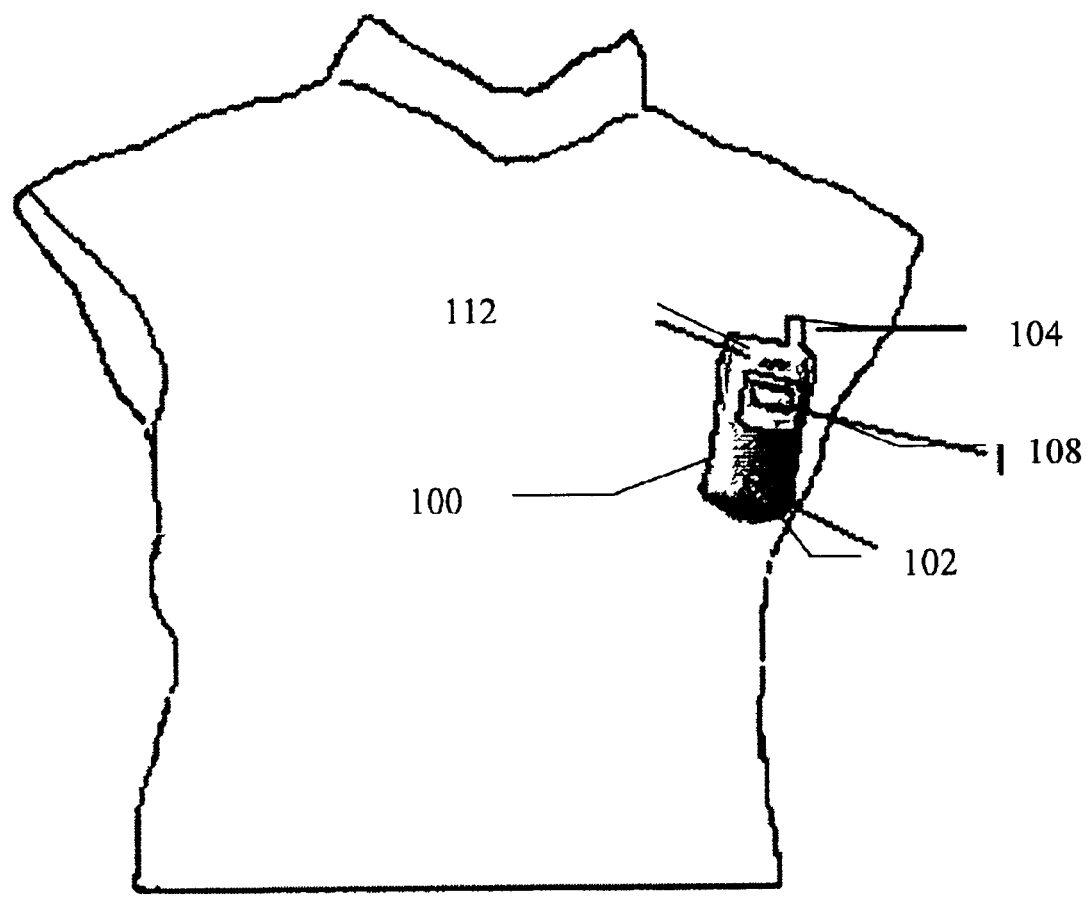
FIG. 13 is a pictographic illustration of a portable monitoring device for use in this invention.
Figure 14:
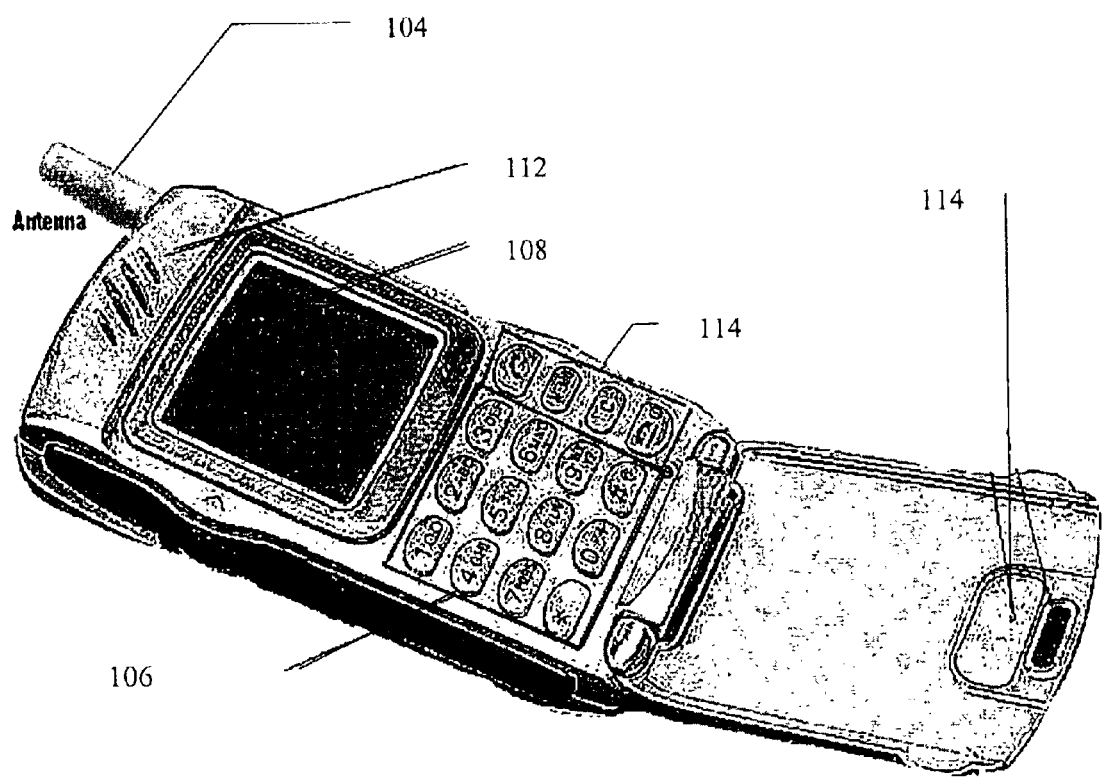
FIG. 14 is pictographic illustration of a portable monitoring device for use in this invention.

Referring to FIG. 11, the same operations as in FIG. 7 are processed by microprocessor 18 under instructions from a program algorithm, in this instance both core and peripheral temperatures being taken and recorded at 52, with the additional operation of determining, as at 93, whether core and peripheral temperature attributes are both moving in the direction of a cut-off attribute, and at 95, ascertaining, as in FIGS. 9 and 10, whether there has been a steep drop in environment temperature. If yes, the same operations as 61 and 63 in FIG. 9 are conducted, which if either are positive, produce an alert signal at 64. If not, the fall of core and peripheral temperatures are not due mainly to a cold environment, and indicate a general failure of the cardiovascular system of the patient, perhaps for the decompensation reasons postulated below. FIG. 12 illustrates the came operations as FIG. 8 with the additional functions of FIG. 11.

In an embodiment of the invention, a mount for external or internal placement of an activity sensor on the patient is provided. The activity sensor detects the patient's activity and outputs signals representative of such activity. The algorithm includes instructions for receiving the signals representative of patient activity and adjusting the signals representative of body temperature of the patient to correct for variation caused by patient activity.

In an embodiment of the invention, there is provided an input modus for adding or modifying information in the program data set. Such input modus allows entering data into the analyzer program data set by which the algorithm is able correct for variation in body temperature caused by one or more factors from among the group consisting essentially of medications, smoking, alcohol use, and solid and/or fluid intake temperature. The algorithm includes instructions for adjusting the signals representative of body temperature of the patient to correct for variation caused by medications, smoking, alcohol use, and solid and/or fluid intake temperature.

Referring to FIGS. 9 and 10, pictographic representations show a device useful in the present invention for monitoring body temperature. The device suitably includes a processing and alarming unit 100 that includes the features of the beltpack device described above in connection with FIGS. 6–8 but adapted in this instance into a size wearable in a shirt-pocket or holster and of about the size of and suitably integrated into a cell phone; a surface and/or implantable temperature sensor 12 (not seen in FIGS. 9 and 10) in communication with unit 100 by wire or wireless transmission, as described in connection with FIGS. 6–8; an external thermosensor and photosensor 102, an internal accelerometer in unit 100 that collects information about the patient's level of activity, and a wireless transceiver communicating using antenna 104. Other features include various input-output devices, such as alphanumeric input devices like a keyboard 106 for data entry and a keyboard 114 for special function inputs, alphanumeric output devices like a monitor 108, and signal output devices such as a beeper alarm for communication by wireless means with the patient or the patient's health caregiver.

From the foregoing, it can be seen that corrections for factors that affect body temperature may be made. A mean, median and standard deviation of temperature recorded in a time stamped and date stamped table can be used to prevent falsing of cutoff points by re-referencing the cut-off points to the patient's own baseline temperature, circadian rhythm, and lunar changes. Additionally taking into account internal and external factors as described above adds additional prognostic value to the criteria used for alerting the patient, the caregiver or a device. Personalized criteria are determined based on preset sensitivity, and corrected values of temperature, and its speed and pattern of change. The preset sensitivity determines cutoff points for speed of temperature change and single temperature measurements, suitably based on Tables 4 and 5. Other information from monitoring and determining a temperature attribute may be used for issuing an alert, such as a pattern of change determined by reckoning the characteristics of interval falls. Interval falls of temperature may be defined as intervals in which temperature is lower than a 24 hr mean, and the characteristics that are important include the maximum amount of fall in the interval, and the interval's duration. Additionally, the frequency of such intervals in a 24 hr period may be considered. As an example, personalized criteria may include: (i) speed of fall larger than the selected cutoff point while corrected for patient's own baseline daily and 28 day variations as well as patient's current status of physical and environmental condition; (ii) interval fall of greater than 1° F. lasting less than 4 hours happening more than 2 times/day while corrected for patient's own baseline daily and 28 day variations as well as patient's current status of physical and environmental condition, and (iii) static temperature less than the selected cutoff point while corrected for patient's own baseline daily and 28 day variations as well as current status of patient's physical and environmental condition.

Without being limited to any particular theory for a mechanism of why very mild hypothermia is an indicator of imminent death in a CHF patient, the following observations are made.

The literature suggests that several competing mechanisms may be operating in the observed temperature decrease. Factors that are expected to decrease temperature in congestive heart failure, as noted in prior reports, are listed in Table 7. These reports also suggest that a number of factors may contribute to the increase in temperature in patients with congestive heart failure, as listed in Table 8.

TABLE 7

Factors That May Decrease Temperature In CHF

Vasodilator therapy
Inactivity
Decreased metabolism due to hypoxemia and severe vasoconstriction
Decreased liver/intestinal metabolism due to venous congestion
Anti-inflammatory effect of hypercortisolemia
Malnutrition
Cell senescence
Down regulation of mitochondrial uncoupling proteins
Down regulation of adenylate cyclase
Down regulation of β adrenergic receptors
Decreased metabolism due to CNS effects of norepinephrine, epinephrine, angiotensin II
Uncoupling of receptors from G proteins
Increased neurotensin

TABLE 8

Factors That May Increase Temperature In CHF

Tachycardia
Tachypnea
Vasoconstriction
"Oxygen-wasting" effect of norepinephrine, epinephrine
$B_3$ adrenergic stimulation
Pyrogenic cytokines (interleukins no 1, 6, 8 and TNF-α)
Oxidation by myocardial macrophages
Increased β adrenergic receptors due to increased cortisol It is not known whether hypothermia adds to a patient's risk of death or whether it is solely a marker of imminent death. The excess vasoconstriction caused by hypothermia may initiate local tissue death, hepatic congestion or a hypothalamic effect. Hypothermia causes an increase in systemic vascular resistance (SVR), which can precipitate or complicate the symptoms of myocardial infarction such as decreased cardiac output (C.O.) and increased pulmonary capillary wedge pressure (PCW). Such effects are known to increase the levels of norepinephrine (NE), angiotensin II (AII), epinephrine (EP), central nervous tissue (CNS), interleukin (IL), tumor necrosis factor (TNF) and the production of reactive oxygen species (ROS). Hypothermia also decreases the myocardial oxygen consumption $M(dot(V) O_2)$.

In the parent patent application, it is proposed that the reasons that some of the CHF patients develop hypothermia at the very end stage of their disease include a decline in heat production due to adrenergic receptor uncoupling, inactivity, anorexia, hypoxemia, and other factors (see Table 7). In addition, since stable CHF patients have relatively higher resting basal metabolic rates and oxidative stress (see Table 8), the bodies of these patients may well use an inefficient f-oxidative pathway (such as glycolysis). Increased lactate level is another indicator that these patients are not using oxygen efficiently. This evidence, considered in light of Shellock F G, Swan H J, Rubin S A, "Muscle and femoral vein temperatures during short-term maximal exercise in heart failure," *J Appl Physiol.* 1985; 58: 400–408, regarding the effects of vasodilators and the core temperature decrease with exercise in heart-failure patients, strongly suggests that in pre-terminal CHF there is decompensation of sympathetic constriction of the peripheral vascular bed. Little by little the warm core blood circulates into cool extremities and muscles resulting in a drop in core temperature. By comparing the peripheral cutaneous temperatures of hypothermic and normothermic patients, it can be determined whether there is relatively more peripheral vasodilation in congestive heart failure patients. A suitable parameter for comparison is the gradient of temperature between peripheral and core areas in the two groups.

Thus, rate of fall of core temperature from the patient's baseline temperature is predictive of imminent death in the patient (i.e., within 24 hours) and suggests a need for intensive medical therapy or consideration for heart transplantation or left ventricular assistance. In addition to the successful intervention in one patient described above, the complications of vasoconstriction caused by cold suggest that hypothermia may not only be a prognostic marker and a stimulus to intervene with medicines, devices or transplantation, but also an indication to warm the patient, indeed recent papers (Tei C, Horikiri Y, Park J C, et al., "Acute hemodynamic improvement by thermal vasodilation in congestive heart failure," *Circulation,* 1995; 91: 2582–2590; and Kihara T, Biro S, Imamura M, et al., "Repeated sauna treatment improves vascular endothelial and cardiac function in patients with chronic heart failure," *J Am Coll Cardiol.,* 2002; 39: 754–759) described an improvement in symptoms when CHF patients (who were not hypothermic) were warmed. These findings differ from the medical literature in that (1) very mild hypothermia, such as was observed in terminal CHF patients, has not been associated with increased mortality (perhaps because most of the patients in those hypothermia reports did not have CHF), and (2) warming did not just relieve symptoms and signs of CHF but also prolonged life.

The following are literature references of interest on congestive heart failure, the more recent of which relate to demographics of CHF, and some of which are about findings that might indirectly and speculatively explain the mechanism, as described above, of hypothermia in CHF or the ill effect of cold on CHF patients. Inclusion of a reference in this list and mention of a reference hereinabove is not intended to suggest or indicate that the reference is prior art to our invention.

1. American Heart Association. 2001 *Heart and Stroke Statistical Update*. Dallas, Tex.: American Heart Association, 2000.
2. McKee P A, Castelli W P, McNamara P M, et al. The natural history of congestive heart failure: the Framingham study. *N Engl J Med.* 1971; 285: 1441–1446.
3. Tsuji H, Larson M G, Venditti F J, et al. Impact of reduced heart rate variability on risk for cardiac events. The Framingham Heart Study. *Circulation.* 1996; 94: 2850–2855.
4. Packer M. Sudden unexpected death in patients with congestive heart failure: a second frontier. *Circulation.* 1985; 72: 681–685.
5. Parameshwar J, Keegan J, Sparrow J, et al. Predictors of prognosis in severe chronic heart failure. *Am Heart J.* 1992; 123: 421–426.
6. Rector T S, Cohn J N. Prognosis in congestive heart failure. *Annu Rev Med.* 1994; 45: 341–350.
7. Gradman A H, Deedwania P C. Predictors of mortality in patients with heart failure. *Cardiol Clin.* 1994; 12: 25–35.
8. Cohn J N, Rector T S. Prognosis of congestive heart failure and predictors of mortality. *Am J Cardiol.* 1988; 62: 25A–30A.
9. Hallstrom A, Pratt C M, Greene H L, et al. Relations between heart failure, ejection fraction arrhythmia suppression, and mortality: analysis of the Cardiac Arrhythmia Suppression Trial. *J Am Coll Cardiol.* 1995; 25: 1250–1257.
10. Cohn J N. Prognostic factors in heart failure: poverty amidst a wealth of variables. *J Am Coll Cardiol.* 1989; 14: 571–572.
11. Siddiqui H, Patel S, Lal B N, et al. Hypothermia: a new indicator of imminent death in congestive heart failure. *J Am Coll Cardiol.* 1999; 33: 212A.
12. Givertz M, Colucci W, Braunwald E. Clinical aspects of heart failure: high-output failure; pulmonary edema. In: Braunwald E, ed. *Heart Disease. A Textbook of Cardiovascular Medicine, 6th ed.* Philadelphia: W B Saunders, 2001:546–549.
13. Adams K F, Dunlap S H, Suteta C A, et al. Relation between gender, etiology and survival in patients with symptomatic heart failure. *J Am Coll Cardiol.* 1996; 28: 1781–1788.
14. Bart B A, Shaw L K, McCants C B, et al. Clinical determinants of mortality in patients with angiographically diagnosed ischemic or nonischemic cardiomyopathy. *J Am Coll Cardiol* 1997; 30: 1002–1008.
15. Szlachic J, Massie B M, Kramer B L, et al. Correlates and prognostic implications of exercise capacity in chronic congestive heart failure. *Am J Cardiol.* 1986; 55: 1037–1042.
16. Chomsky D B, Lang C C, Rayos G H, et al. Hemodynamic exercise testing: a valuable tool in the selection of cardiac transplantation candidates. *Circulation.* 1996; 94: 3176–3183.
17. Lanfranchi P A, Braghiroli A, Bosimini E, et al. Prognostic value of nocturnal Cheyne-Stokes respiration in chronic heart failure. *Circulation.* 1999; 99: 1435–1440.
18. Anker S D, Ponikowski P, Varney S, et al. Wasting as independent risk factor for mortality in chronic heart failure. *Lancet.* 1997; 349: 1050–1053.
19. Anguita M, Arizon J M, Bueno G, et al. Clinical and hemodynamic predictors of survival in patients aged <65 years with severe congestive heart failure secondary to ischemic or nonischemic dilated cardiomyopathy. *Am J Cardiol.* 1993; 72: 413–417.
20. Bittner V, Weiner D H, Yusuf S, et al. Prediction of mortality and morbidity with a 6-minute walk test in patients with left ventricular dysfunction. SOLVD Investigators. *JAMA.* 1993; 13: 1702–1707.
21. Gradman A, Deedwania P, Cody R, et al. Predictors of total mortality and sudden death in mild to moderate heart failure. Captopril-Digoxin Study Group. *J Am Coll Cardiol.* 1989; 14: 564–570.
22. de Groote P, Millaire A, Foucher-Hossein C, et al. Right ventricular ejection fraction is an independent predictor of survival in patients with moderate heart failure. *J Am Coll Cardiol.* 1998; 32: 948–954.
23. Myers J, Gullestad L, Vagelos R, et al. Clinical, hemodynamic, and cardiopulmonary exercise test determinants of survival in patients referred for evaluation of heart failure. *Ann Intern Med.* 1998; 15: 286–293.
24. Cohn J N, Levine T B, Olivari M T, et al. Plasma norepinephrine as a guide to prognosis in patients with chronic congestive heart failure. *N Engl J Med.* 1984; 311: 819–823.
25. Francis G S, Cohn J N, Johnson G, et al. Plasma norepinephrine, plasma renin activity, and congestive heart failure: Relations to survival and the effects of therapy in V-HeFT II. The V-HeFT VA Cooperative Studies Group. *Circulation.* 1993; 87(Suppl 6): VI40–VI48.
26. Hulsmann M, Stanek B, Frey B, et al. Value of cardiopulmonary exercise testing and big endothelin plasma levels to predict short-term prognosis of patients with chronic heart failure. *J Am Coll Cardiol.* 1998; 32: 1695–1700.
27. Tsutamoto T, Hisanaga T, Wada A, et al. Interleukin-6 spillover in the peripheral circulation increases with the severity of heart failure, and the high plasma level of interleukin-6 is an important prognostic predictor in patients with congestive heart failure. *J Am Coll Cardiol.* 1998; 31: 391–398.
28. Packer M. Potential role of potassium as a determinant of morbidity and mortality in patients with systemic hypertension and congestive heart failure. *Am J Cardiol.* 1990; 65: 45E–52E.
29. Dargie H J, Cleland J G, Leckie B J, et al. Relation of arrhythmias and electrolyte abnormalities to survival in patients with severe chronic heart failure. *Circulation.* 1987; 75: IV98–IV107.
30. Dries D L, Exner D V, Gersh B J, et al. Atrial fibrillation is associated with an increased risk for mortality and heart failure progression in patients with asymptomatic and symptomatic left ventricular systolic dysfunction: a retrospective analysis of the SOLVD trials. *J Am Coll Cardiol.* 1998; 32: 695–703.
31. Klingenheben T, Zabel M, D'Agostino R B, et al. Predictive value of T-wave alternans for arrhythmic events in patients with congestive heart failure. *Lancet.* 2000; 356: 651–652.
32. Anastasiou-Nana M I, Nanas J N, Karagounis L A, et al. Relation of dispersion of QRS and QT in patients with advanced congestive heart failure to cardiac and sudden death mortality. *Am J Cardiol.* 2000; 85: 1212–1217.
33. Deng M C, De Meester J M, Smits J M, Heinecke J, Scheld H H. Effect of receiving a heart transplant: analysis of a national cohort entered on to a waiting list, stratified by heart failure severity. Comparative Outcome and Clinical Profiles in Transplantation (COCPIT) Study Group. *BMJ* 2000; 321: 540–545.

34. Whittle J L, Bates J H. Thermoregulatory failure secondary to acute illness: complications and treatment. *Arch Intern Med.* 1979; 139: 418–421.
35. Blum A, Miller H. Pathophysiological role of cytokines in congestive heart failure. *Annu Rev Med.* 2001; 52: 15–27.
36. Weg J G. Oxygen transport in adult respiratory distress syndrome and other acute circulatory problems: relationship of oxygen delivery and oxygen consumption. Crit Care Med 1991 May;19(5):650–7.
37. Shibutani K, Komatsu T, Kubal K, Sanchala V, Kumar V, Bizzarri D V. Critical level of oxygen delivery in anesthetized man. Crit Care Med 1983 Aug; 11(8):640–3.
38. Zeisberger E. The roles of monoaminergic neurotransmitters in thermoregulation. *Can J Physiol Pharmacol.* 1987; 65: 1395–1401.
39. Poehlman E T, Scheffers J, Gottlieb S S, et al. Increased resting metabolic rate in patients with congestive heart failure. *Ann Intern Med.* 1994; 121: 860–862.
40. Shellock F G, Swan H J, Rubin S A. Muscle and femoral vein temperatures during short-term maximal exercise in heart failure. *J Appl Physiol.* 1985; 58: 400–408.
41. Brengelmann G L. Body temperature regulation in heart failure. *Cardiologia.* 1996; 41: 1033–1043.
42. Westheim A, Os I, Thaulow E, et al. Haemodynamic and neurohumoral effects of cold pressor test in severe heart failure. *Clin Physiol.* 1992; 12: 95–106.
43. Rodriguez-Garcia J L, Paule A, Dominguez J, et al. Effects of the angiotensin II antagonist losartan on endothelin-1 and norepinephrine plasma levels during cold pressor test in patients with chronic heart failure. *Int J Cardiol.* 1999; 70: 293–301.
44. Lassvik C T, Areskog N. Angina in cold environment. Reactions to exercise. *Br Heart J.* 1979; 42: 396–401.
45. Cohn J N, Ferrari R, Sharpe N. Cardiac remodeling— concepts and clinical implications: a consensus paper from an international forum on cardiac remodeling. *J Am Coll Cardiol.* 2000; 35: 569–582.
46. Givertz M M, Colucci W S. New targets for heart failure therapy: endothelin, inflammatory cytokines and oxidative stress. *Lancet.* 1998; 352(Suppl 1): SI34–SI38.
47. Astrup P, Engel K, Severinghaus J W, et al. The influence of temperature and pH on the dissociation curve of oxyhemoglobin of human blood. Scand J Clin Lab Invest. 1965; 17: 515–523.
48. Tei C, Horikiri Y, Park J C, et al. Acute hemodynamic improvement by thermal vasodilation in congestive heart failure. Circulation. 1995; 91: 2582–2590.
49. Kihara T, Biro S, Imamura M, et al. Repeated sauna treatment improves vascular endothelial and cardiac function in patients with chronic heart failure. J Am Coll Cardiol. 2002; 39: 754–759.
50. Jurkovich G J, Greiser W B, Luterman A, Curreri P W. Hypothermia in trauma victims: an ominous predictor of survival. J Trauma 1987 September;27(9):1019–24
51. Gentilello L M, Jurkovich G J, Stark M S, Hassantash S A, O'Keefe G E. Is hypothermia in the victim of major trauma protective or harmful? A randomized, prospective study. Ann Surg 1997 October; 226(4):439–47; discussion 447–9

Having described our discovery and methodology, means, apparatus and systems for implementations of that discovery in aid of the CHF patient, our invention is not to be limited only to the particular embodiments detailed but includes implementations within the spirit and scope of the invention, as set forth in the following claims, and equivalents of elements of the claims.

What is claimed is:

1. A method alerting a worsening of condition in a patient with congestive heart failure, which comprises:
    (a) pre-setting a cut-off point of at least one temperature attribute of hypothermia comprising rate of fall of body temperature relative to optimum sensitivity and specificity for such attribute as a congestive heart failure predictor of death of a patient,
    (b) routinely determining that attribute in the patient, and
    (c) determining from said routine determinations of said attribute whether a condition of congestive heart failure hypothermia has occurred, and if so,
    (d) issuing an alert warning of said worsening condition.

2. The method of claim 1 in which said operation (c) comprises determining whether said attribute has attained or crossed said cut-off point.

3. The method of claim 1 further comprising routinely determining said attribute for at least one peripheral site and for a core site and in which said operation (c) comprises determining whether said attribute in both said sites are moving in the direction of said cut-off point.

4. The method of claim 1 in which said operation (c) comprises determining whether rise of core temperature of the patient from a temperature below a baseline temperature of the patient to a temperature at or closer to baseline lags behind rise of core temperature of the normal person from a temperature below a baseline temperature of the normal person to a temperature at or closer to baseline, or if the core temperature of the patient rises from a temperature below a baseline temperature of the patient to less than a predetermined minimum acceptable rise.

5. A method caring for a patient with congestive heart failure, which comprises:
    (a) pre-setting a cut-off point of at least one temperature attribute of hypothermia comprising rate of fall of body temperature relative to optimum sensitivity and specificity for such attribute as a congestive heart failure predictor of death of a patient,
    (b) routinely determining that attribute in the patient, and
    (c) determining whether said attribute has attained or crossed said cut-off point.

6. The method of claim 5 in which optimum sensitivity and specificity for rate of fall of body temperature is 0.4° F. per hour.

7. The method of claim 5 in which said temperature attribute additionally comprises a hypothermic body temperature.

8. The method of claim 7 in which optimum sensitivity and specificity for hypothermic body temperature is 95° F.

9. The method of claim 5 in which said cut-off point is pre-set as (i) the optimum sensitivity and specificity value of said temperature attribute, (ii) an increase in the sensitivity of said cut-off point from the optimum sensitivity and specificity value of said temperature attribute, or (iii) a decrease in the sensitivity of said cut-off point from the optimum sensitivity and specificity value of said temperature attribute.

10. The method of claim 5 further comprising:
    (d) outputting an alert if said temperature attribute has attained or crossed said cut-off point.

11. The method of claim 10 in which said alert is output at least to the patient.

12. The method of claim 10 in which said alert is output at least to a healthcare provider.

13. The method of claim 10 in which said alert is output at least to a device.

14. The method of claim 13 in which said device is a medical device that applies a therapeutic treatment to said patient to treat the patient's condition of congestive heart failure.

15. The method of claim 14 in which said device is a ventricular assist device responsive to said alert to provide additional ventricular assist to the patient.

16. The method of claim 14 in which said device is a medication release device responsive to said alert to adjust the amount of medication the patient is receiving.

17. The method of claim 14 in which said device is a cardiac rhythmic regulator, responsive to said alert to optimize the patient's regulator parameters to reverse hypothermia.

18. The method of claim 14 in which said device is responsive to said alert to warm the patient.

19. The method of claim 10 in which the cut-off point is a selected increase or decrease of sensitivity of said cut-off point from said optimum specificity and sensitivity value of said temperature attribute, chosen to output an alert at a time that best suits the patient's condition considering at least one of (a) at least one prognostic factor other than said temperature attribute, (b) at least one co-morbidity, and (c) availability of immediate care by a healthcare provider.

20. The method of claim 19 in which said at least one prognostic factor is selected from chest impedance peak oxygen uptake (dot(V)O2), left and right ventricular ejection function, both respiratory and circulatory response to exercise, cardiac index, left ventricular cavity size, left ventricular stroke work index, right and left ventricular filling pressure, left ventricular filling isovolumic relaxation time, left ventricular systolic pressure, right and left atrial pressure, systemic vascular resistance, calculated wall stress, tricuspid regurgitation, jugular venous pressure, pulmonary capillary wedge pressure, 6-minute walk distance, arterial and venous pH, pO2, pCO2, serum creatinine, serum sodium, plasma norepinephrine, plasma neurotensin, plasma renin activity, plasma arginine vasopressin, plasma atrial and brain natriuretic peptides, plasma endothelin-1, plasma interleukin-6, plasma tumor necrosis-alpha, serum sodium, serum potassium, total potassium stores, serum magnesium, lymphocyte count, frequent ventricular extrasystoles, ventricular tachycardia, left bundle-branch blockage, right bundle-branch blockage, atrial fibrillation or flutter, T-wave alternans, QT prolongation, QT dispersion, age, sex, ischemic heart disease, New York Hear Association functional class, S3 gallop, Cheyne-Stokes respiration, apnea/hypopnea index, systolic blood pressure, heart rate at rest, pulse pressure, mean arterial pressure, and cardiac cachexia.

21. The method of claim 20 in which at least one of the prognostic factors is present, and comprising pre-setting said cut-off point at an increased sensitivity of said temperature attribute from the optimum sensitivity and specificity for that temperature attribute.

22. The method of claim 19 in which said co-morbidity is any of (a) Alzheimer's disease or other dementia, (b) depressive mood, and (c) motor disability, and wherein output of said alert is directed to at least to a healthcare provider.

23. The method of claim 19 in which availability of immediate care by a healthcare provider includes care available (i) as intensive care, (ii) as in-patient care not intensive care, (iii) as care within up to about 24 hours for an out-patient, and (iv) as care with more than about 24 hours delay for an out-patient, and comprising pre-setting said temperature attribute cut-off point in a range from a larger decrease, for care available as intensive care, to an larger increase, for care available with more than 24 hours delay, from optimum sensitivity and specificity for that temperature attribute.

24. The method of claim 5 further comprising determining and making adjustments of said periodically determined temperature attributes or said cut-off point on the basis of one or more of the patient's environmental temperature and light.

25. The method of claim 5 further comprising determining and making adjustments of said periodically determined temperature attributes or said cut-off point on the basis of one or more of the patient's activity, medications, smoking, alcohol use, and solid and/or fluid intake temperature.

26. The method of claim 10, comprising periodically ascertaining body temperature, and further comprising
    (e) determining maximum amount of body temperature fall in a selected interval, the interval's duration and the frequency of such intervals, to define a set,
    (f) determining whether said set exceeds limits of at least one predefined pattern of maximum amount of body temperature fall in a selected interval, the interval's duration and the frequency of such intervals, and if so,
    (g) outputting an alert.

27. The method of claim 10 in which said cut-off point is referenced to normal body temperature, and further comprising determining a selected measure of central tendency and measure of dispersion of the patient's body temperatures to define the patient's own baseline body temperature.

28. The method of claim 27, further comprising:
    (e) re-referencing said cut-off point from said normal body temperature to said baseline body temperature, and
    (f) determining whether said temperature attribute of hypothermia has attained or crossed said re-referenced cut-off point, and if so,
    (g) outputting an alert.

29. The method of claim 28, comprising periodically ascertaining body temperature, and further comprising
    (h) ascertaining body temperatures at intervals in which such temperatures are lower than said baseline temperature, to define a set,
    (i) determining whether said set exceeds limits of at least one predefined pattern of maximum amount of body temperature fall in a selected interval, the interval's duration and the frequency of such intervals, and if so,
    (j) outputting an alert.

30. The method of claim 5 further comprising routinely determining said attribute for at least one peripheral site and for a core site and determining whether said attribute in both said sites is moving in the direction of said cut-off point, and if so, outputting an alert.

31. A method of monitoring and warning of worsening of condition of congestive heart failure in a patient, which comprises:
    (a) pre-setting a cut-off point of at least one temperature attribute of hypothermia comprising rate of fall of body temperature relative to optimum sensitivity and specificity for that temperature attribute as a congestive heart failure predictor of death of a patient, referenced to normal body temperature,
    (b) routinely determining a selected measure of central tendency and measure of dispersion of body temperatures to define the patient's own baseline body temperature,
    (c) re-referencing said cut-off point from said normal body temperature to said baseline body temperature, and (d) routinely determining whether said temperature attribute has attained or crossed said cut-off point before and after said re-referencing, and if so, outputting an alert.

32. A method of monitoring and warning of worsening of condition of congestive heart failure in a patient, which comprises:
(a) pre-setting a cut-off point of at least one temperature attribute of hypothermia comprising rate of fall of body temperature relative to optimum sensitivity and specificity for that temperature attribute as a congestive heart failure predictor of death of a patient, referenced to normal body temperature,
(b) ascertaining body temperatures of the patient in intervals of time,
(c) determining whether said temperature attribute has attained or crossed said cut-off point, and if so, outputting an alert,
(d) determining a selected measure of central tendency and measure of dispersion of body temperatures to define the patient's own baseline body temperature,
(e) re-referencing each said cut-off point from said normal body temperature to said baseline body temperature, and
(f) determining whether said temperature attribute has attained or crossed said re-referenced cut-off point, and if so, outputting an alert.

33. The method of claim 32 further comprising determining adjustments of said ascertained body temperatures on the basis of one or more of the patient's environmental temperature and light.

34. The method of claim 32 further comprising determining adjustments of said ascertained body temperatures on the basis of one or more of the patient's activity, medications, smoking, alcohol use, and solid and/or fluid intake temperature.

35. The method of claim 34 further comprising determining adjustments of said ascertained body temperatures on the basis of one or more of the patient's environmental temperature and light.

36. A method of monitoring and warning of worsening of condition of congestive heart failure in a patient, which comprises:
(a) setting a cut-off point for temperature and rate of fall of temperature as temperature attributes of hypothermia relative to optimum sensitivity and specificity for those temperature attributes as a congestive heart failure predictor of death of a patient, basis normal body temperature,
(b) ascertaining body temperatures of the patient in intervals of time,
(c) determining whether a said temperature attribute has attained or crossed said cut-off point, and if so outputting an alert thereof,
(d) determining maximum amount of body temperature fall in a selected interval, the interval's duration and the frequency of such intervals, as a set,
(e) determining whether said set exceeds limits of at least one predefined pattern of maximum amount of body temperature fall in a selected interval, the interval's duration and the frequency of such intervals, and if so, outputting an alert,
(f) determining a selected measure of central tendency and measure of dispersion of body temperatures to define the patient's own baseline body temperature,
(g) re-referencing each said cut-off point and said predefined pattern limits from said normal body temperature to said baseline body temperature,
(h) determining whether said temperature attribute has attained or crossed said re-referenced cut-off point, and if so, outputting an alert, and
(i) determining whether said set exceeds said re-referenced predefined pattern limits, and if so, outputting an alert.

37. A method of monitoring and warning of worsening of condition of congestive heart failure in a patient, which comprises:
(a) monitoring and recording environmental temperature and core temperature of the patient,
(b) determining whether a steep fall in environmental temperature has occurred, and if so,
(c) comparing the patient's core temperature and the patient's change in core temperature over time to a core temperature and a change in core temperature over time of a normal person at environmental temperatures monitored beginning with the temperatures included in said steep fall, and
(d) issuing an alert if rise of core temperature of the patient from a temperature below a baseline temperature of the patient to a temperature at or closer to baseline lags behind rise of core temperature of the normal person from a temperature below a baseline temperature of the normal person to a temperature at or closer to baseline, or if the core temperature of the patient rises from a temperature below a baseline temperature of the patient to less than a predetermined minimum acceptable rise.

38. Apparatus for monitoring a patient with congestive heart failure for worsening of condition thereof, which comprises:
(a) means for pre setting a cut-off point of at least one temperature attribute of hypothermia comprising rate of fall of body temperature relative to optimum sensitivity and specificity for that temperature attribute as a congestive heart failure predictor of death of a patient,
(b) means for routinely determining that temperature attribute of the patient, and
(c) means for determining whether said temperature attribute has attained or crossed said cut-off point.

39. The apparatus of claim 38 in which optimum sensitivity and specificity for rate of fall of body temperature of 0.4° F. per hour.

40. The apparatus of claim 38 in which said temperature attribute also comprises a hypothermic body temperature of the patient.

41. The apparatus of claim 38 in which optimum sensitivity and specificity for hypothermic body temperature is 95° F.

42. The apparatus of claim 38 further comprising means for routinely determining said at least one attribute at least one peripheral site and at a core site of the patient and for determining whether said at least one attribute in both said sites are moving in the direction of said cut-off point, and if so, outputting an alert.

43. The apparatus of claim 38 in which said cut-off point is pre-set as (i) the optimum sensitivity and specificity value of said temperature attribute, (ii) an increase in the sensitivity of said cut-off point from the optimum sensitivity and specificity value of said temperature attribute, or (iii) a decrease in the sensitivity of said cut-off point from the optimum sensitivity and specificity value of said temperature attribute.

44. The apparatus of claim 38 further comprising:
(d) means for outputting an alert operative on the condition that said temperature attribute has attained or crossed said cut-off point.

45. The apparatus of claim 44 in which said alert is output at least to the patient.

46. The apparatus of claim 44 in which said alert is output at least to a healthcare provider.

47. The apparatus of claim 44 in which said alert is output at least to a device.

48. The apparatus of claim 47 in which said device is a medical device that applies a therapeutic treatment to said patient to treat the patient's condition of congestive heart failure.

49. The apparatus of claim 48 in which said device is a ventricular assist device responsive to said alert to provide additional ventricular assist to the patient.

50. The apparatus of claim 48 in which said device is an intravenous infusion device responsive to said alert to adjust the amount of medication the patient is receiving.

51. The apparatus of claim 48 in which said device is a cardiac rhythmic regulator, responsive to said alert to optimize the patient's regulator parameters to reverse hypothermia.

52. The apparatus of claim 48 in which said device is responsive to said alert to warm the patient.

53. The apparatus of claim 44 in which the cut-off point is a selected increase or decrease of sensitivity of said cut-off point from said optimum specificity and sensitivity value of said temperature attribute, chosen to output an alert at a time that best suits the patient's condition considering at least one of (a) at least one prognostic factor other than said temperature attribute, (b) at least one co-morbidity, and (c) availability of immediate care by a healthcare provider.

54. The apparatus of claim 53 in which said at least one prognostic factor is selected from any of chest impedance peak oxygen uptake (dot(V)O2), left and right ventricular ejection function, both respiratory and circulatory response to exercise, cardiac index, left ventricular cavity size, left ventricular stroke work index, right and left ventricular filling pressure, left ventricular filling isovolumic relaxation time, left ventricular systolic pressure, right and left atrial pressure, systemic vascular resistance, calculated wall stress, tricuspid regurgitation, jugular venous pressure, pulmonary capillary wedge pressure, 6-minute walk distance, arterial and venous pH, pO2, pCO2, serum creatinine, serum sodium, plasma norepinephrine, plasma neurotensin, plasma renin activity, plasma arginine vasopressin, plasma atrial and brain natriuretic peptides, plasma endothelin-1, plasma interleukin-6, plasma tumor necrosis-alpha, serum sodium, serum potassium, total potassium stores, serum magnesium, lymphocyte count, frequent ventricular extrasystoles, ventricular tachycardia, left bundle-branch blockage, right bundle-branch blockage, atrial fibrillation or flutter, T-wave alternans, QT prolongation, QT dispersion, age, sex, ischemic heart disease, New York Hear Association functional class, S3 gallop, Cheyne-Stokes respiration, apnea/hypopnea index, systolic blood pressure, heart rate at rest, pulse pressure, mean arterial pressure, and cardiac cachexia.

55. The apparatus of claim 44 further comprising means for determining adjustments of said determined at least one temperature attribute on the basis of one or more of the patient's environmental temperature and light.

56. The apparatus of claim 44 further comprising means for determining adjustments of said determined at least one temperature attribute on the basis of one or more of the patient's activity, medications, smoking, alcohol use, and solid and/or fluid intake temperature.

57. The apparatus of claim 44 in which said means for routinely determining said temperature attribute comprises means for ascertaining the body temperature of the patient and means for determining maximum amount of body temperature fall in a selected interval, the interval's duration and the frequency of such intervals, as a set, said apparatus further comprises means for determining whether said set exceeds limits of a predefined pattern of maximum amount of body temperature fall in a selected interval, the interval's duration and the frequency of such intervals.

58. The apparatus of claim 44 in which said means for routinely determining said temperature attribute comprises means for ascertaining the body temperature of the patient and means for determining a selected measure of central tendency and measure of dispersion of the patient's body temperatures to define the patient's own baseline body temperature.

59. The apparatus of claim 58, in which said means for routinely determining said temperature attribute further comprises means for re-referencing said cut-off point from said normal body temperature to said baseline body temperature.

60. The apparatus of claim 59 in which said means for routinely determining said temperature attribute further comprises means for ascertaining the body temperature of the patient and means for determining maximum amount of body temperature fall in a selected interval, the interval's duration and the frequency of such intervals, as a set, said apparatus further comprises means for determining whether said set exceeds limits of a predefined pattern of maximum amount of body temperature fall in a selected interval, the interval's duration and the frequency of such intervals.

61. Apparatus for monitoring and warning of worsening of condition of congestive heart failure in a patient, which comprises:
(a) means for pre-setting a cut-off point of at least one temperature attribute of hypothermia comprising rate of fall of body temperature relative to optimum sensitivity and specificity for that temperature attribute as a congestive heart failure predictor of death of a patient, referenced to normal body temperature,
(b) means for determining body temperature of the patient in intervals of time,
(c) means for routinely determining a selected measure of central tendency and measure of dispersion of body temperatures to define the patient's own baseline body temperature,
(d) means for re-referencing each said cut-off point from said normal body temperature to said baseline body temperature, and
(e) means for routinely determining whether said temperature attribute has attained or crossed said cut-off point before and after said re-referencing, and
(f) means for outputting an alert on condition that said temperature attribute has attained or crossed said cut-off point before and after said re-referencing.

62. The apparatus of claim 61 further comprising means for adjusting said body temperatures on the basis of one or more of the patient's environmental temperature and light.

63. The apparatus of claim 61 further comprising means for adjusting said body temperatures on the basis of one or more of the patient's activity, medications, smoking, alcohol use, and solid and/or fluid intake temperature.

64. The apparatus of claim 63 further comprising means for adjusting said body temperatures on the basis of one or more of the patient's environmental temperature and light.

65. Apparatus for monitoring and warning of worsening of condition of congestive heart failure in a patient, which comprises:
(a) means for setting a cut-off point for temperature and rate of fall of temperature as temperature attributes of hypothermia relative to optimum sensitivity and specificity for those temperature attribute as a congestive heart failure predictor of death of a patient, referenced to normal body temperature,
(b) means for ascertaining body temperatures of the patient in intervals of time
(c) means for determining said temperature attributes of the patient at predetermined intervals of time,
(d) means for determining whether a said temperature attribute has attained or crossed said cut-off point,
(e) means for determining maximum amount of body temperature fall in a selected interval, the interval's duration and the frequency of such intervals, as a set,
(f) means for determining whether said set exceeds limits of a predefined pattern of maximum amount of body temperature fall in a selected interval, the interval's duration and the frequency of such intervals,
(g) means for determining a selected measure of central tendency and measure of dispersion of the patient's body temperatures to define the patient's own baseline body temperature,
(h) means for re-referencing each said cut-off point and said predefined pattern limits from said normal body temperature to said baseline body temperature,
(i) means for determining whether a said temperature attribute of hypothermia has attained or crossed said re-referenced cut-off point,
(j) means for determining whether a said set exceeds said re-referenced predefined pattern limits, and
(k) means for outputting an alert on condition of a said temperature attribute has attained or crossed said cut-off point before or after a re-referencing of each said cut-off point to said baseline temperature, and on condition of a said set exceeding said predefined pattern limits before or after re-referencing said predefined pattern limits to said baseline temperature.

66. The apparatus of claim 65 further comprising means for adjusting said ascertained body temperatures on the basis of one or more of the patient's environmental temperature and light.

67. The apparatus of claim 65 further comprising means for adjusting said ascertained body temperatures on the basis of one or more of the patient's activity, medications, smoking, alcohol use, and solid and/or fluid intake temperature.

68. The apparatus of claim 67 further comprising means for adjusting said ascertained body temperatures on the basis of one or more of the patient's environmental temperature and light.

69. Apparatus monitoring and warning of worsening of condition of congestive heart failure in a patient, comprising:
(a) a temperature sensor for sensing body temperatures of a patient and outputting signals representative of the sensed temperatures,
(b) a mount of said temperature sensor for indwelling or external placement on the patient,
(c) an analyzer including a digital signal processor, program memory and data memory,
(d) said program memory containing a program data set having a cut-off point for at least rate of fall of body temperature as a temperature attribute of hypothermia point relative to optimum sensitivity and specificity for such temperature attribute as a congestive heart failure predictor of death of a patient,
(e) an algorithm in said program memory for instructing said processor to perform functions including periodically writing to said data memory data based on said temperature representation signals and reading data from said data memory, and periodically comparing data from data memory with data in said program data set to determine whether a temperature attribute including at least rate of fall of body temperature has attained or crossed said cut-off point, and if so, outputting a signal indicative of cut-off point attainment or crossover, and
(f) an alarm for receiving said output signal from said processor and expressing an alert.

70. The apparatus of claim 69 in which said data periodically written and read to and from said data memory includes body temperature, and said cut-off point in said program memory set includes a body temperature cut-off point.

71. The apparatus of claim 69 in which said data periodically written and read to and from said data memory includes a calculated rate of fall of body temperature.

72. The apparatus of claim 69 in which said algorithm includes instructions for instructing said processor to determine a selected measure of central tendency and measure of dispersion of patient body temperature to define the patient's own baseline body temperature, and to re-reference said cut-off point to said baseline body temperature.

73. The apparatus of claim 69 in which said program data set is further characterized as comprising a range of sensitivity and specificity pairs, each pair having a cut-off point for at least one temperature attribute of hypothermia as a congestive heart failure predictor of death of a patient, said range including a sensitivity and a specificity pair for an optimal cut-off point of said temperature attribute, and wherein said apparatus further comprises an adjuster communicable with said analyzer for pre-setting a said cut-off point relative to optimum sensitivity and specificity for that temperature attribute in said program data set.

74. The apparatus of claim 69 in which said program data set includes data comprising a predefined limit pattern of maximum amount of body temperature fall in a selected interval, the interval's duration and the frequency of such intervals, and wherein said algorithm includes instructions for instructing said processor (i) to periodically determine the maximum amount of body temperature fall in a selected interval, the interval's duration, and the frequency of such intervals, as a set, (ii) to determine whether said set exceeds said limit pattern in said program data set, and if so, (iii) to output a signal indicative of attainment or crossover of said limit pattern.

75. The apparatus of claim 69 further comprising
(i) a sensor for detecting an environmental factor affecting patient temperature and outputting signals representative of the sensed environmental factor, and
(j) a mount for said environmental factor sensor for external placement on the patient; and
wherein said algorithm includes instructions for receiving such signals representative of the sensed environmental factor and adjusting said signals representative of body temperature of the patient to correct for variation caused by said environmental factor.

76. The apparatus of claim 69 further comprising
(i) an activity sensor for detecting the patient's activity and outputting signals representative of such activity, (j) a mount for said activity sensor for external or internal placement on the patient, and wherein said algorithm includes instructions for receiving said signals representative of patient activity and adjusting said signals representative of body temperature of the patient to correct for variation caused by patient activity.

77. The apparatus of claim 69 further comprising an input for adding or modifying information in said program data set.

78. The apparatus of claim 69 further comprising (i) an input for entering data into said analyzer program data set by which said algorithm is able correct for variation in body temperature caused by one or more factors from among the group consisting essentially of medications, smoking, alcohol use, and solid and/or fluid intake temperature, and wherein said algorithm includes instructions for adjusting said signals representative of body temperature of the patient to correct for variation caused by medications, smoking, alcohol use, and solid and/or fluid intake temperature.

79. The apparatus of claim 69 in which said mount is an indwelling medical device selected from the group consisting of an implanted capsule, a needle, tube, catheter, line, pacemaker, implanted pump and implanted defibrillator.

80. The apparatus of claim 79, wherein said tube is selected from the group consisting of a nasogastric tube, Dubbhoff tube, endotracheal tube, rectal tube, T-tubes, drain, and nasal probe.

81. The apparatus of claim 79, wherein said catheter is selected from the group consisting of a urinary catheter, pulmonary artery catheter, triple-lumen catheter, dialysis catheter, Hickman catheter, and infusion catheter.

82. The apparatus of claim 69, wherein said mount for external placement is selected from the group consisting of umbilical sensor, skin electrode, tympanic ear sensor, pulse oximeter, and casts.

83. The apparatus of claim 69 in which said temperature sensor is selected from the group consisting of a thermocouple, thermistor, thermosensitive chromophore, thermosensitive liquid crystal, infrared detector and ultrasound detector.

84. The apparatus of claim 69 in which said alert is a text display, sound, shock, change in color or shape, warmth, or vibration.

85. The apparatus of claim 69 in which said mount for said temperature sensor is a hearing aid.

86. The apparatus of claim 69 in which said mount for said sensor is wearable on the wrist of the patient.

87. The apparatus of claim 86 in which said wearable mount is a wrist watch into which the temperature sensor and said analyzer is integrated.

88. The apparatus of claim 69 further comprising a signal conditioner for preparing said signals representative of the sensed temperatures for use by said analyzer.

89. The apparatus of claim 88 in which said temperature sensor includes an infrared sensor mountable in an ear of a patient for sensing infrared radiation from tympanic membrane perfusion, and wherein said signal conditioner includes an infrared detector located remotely from the sensor and connected to the sensor by a cable, said signal conditioner further comprising a transducer for converting an analog signal to a digital signal representative of the body temperature sensed by said infrared sensor.

90. The apparatus of claim 89 in which said cable is an electrical cable and said signal is an electrical signal.

91. The apparatus of claim 89 in which said cable is an optical cable, said analog signal is an optical signal, and said digital signal is an electrical signal.

92. The apparatus of claim 89 in which said temperature sensor is a cholesteric crystal mountable on the skin of a patient, and wherein said signal conditioner includes:

an optical color illuminator and detector for illuminating said crystal and detecting spectral changes in said crystal as a result of change of temperature of the crystal and converting said detected changes to a digital signal for transmission to said analyzer, and a fiber optic cable connecting said cholesteric crystal to said optical color illuminator and detector.

93. The apparatus of claim 89 in which said temperature sensor is a thermistor mountable on the skin of a patient, and wherein said signal conditioner comprises an amplifier and transducer for amplifying and converting an analog signal to a digital signal representative of the body temperature sensed by said thermistor.

94. The apparatus of claim 89 in which said temperature sensor is a temperature controlled oscillator implantable in the patient, and wherein said signal conditioner comprises a radio frequency transceiver for receiving wireless analog signals and transducing analog signals to digital signals representative of the body temperature sensed by said oscillator.

95. The apparatus of claim 69 in which said alert is output at least to the patient.

96. The apparatus of claim 69 in which said alert is output at least to a healthcare provider.

97. A system for monitoring and treating a congestive heart failure patient for worsening congestive heart failure, comprising:

(a) a temperature sensor for sensing body temperatures of a patient and outputting signals representative of the sensed temperatures, (b) a mount of said temperature sensor for indwelling or external placement on the patient, (c) an analyzer including a digital signal processor, program memory and data memory, (d) said program memory containing a program data set having a cut-off point for at least rate of fall of body temperature as a temperature attribute of hypothermia point relative to optimum sensitivity and specificity for such temperature attribute as a congestive heart failure predictor of death of a patient, (e) an algorithm in said program memory for instructing said processor to perform functions including periodically writing to said data memory data based on said temperature representation signals and reading data from said data memory, and periodically comparing data from data memory with data in said program data set to determine whether a temperature attribute including at least rate of fall of body temperature has attained or crossed said cut-off point, and if so, outputting a signal indicative of cut-off point attainment or crossover, (f) a notifier for receiving said output signal from said processor and sending a notifying signal, and (g) a device responsive to said notification signal for applying a therapeutic treatment to said patient to treat the patient's condition of congestive heart failure.

98. The system of claim 97 in which said device is a ventricular assist device responsive to said notifying signal to provide additional ventricular assist to the patient.

99. The system of claim 97 in which said device is an intravenous infusion device responsive to said notifying signal to adjust the amount of medication the patient is receiving.

100. The system of claim 97 in which said device is a cardiac rhythmic regulator, responsive to said notifying signal to optimize the patient's regulator parameters to reverse hypothermia.

101. The system of claim 97 in which said device is responsive to said notifying signal to warm the patient.

102. Apparatus for monitoring and warning of worsening of condition of congestive heart failure in a patient, which comprises:

(a) means for monitoring and recording environmental temperature and core temperature of the patient, (b) means for determining whether a steep fall in environmental temperature has occurred, and if so, (c) means comparing the patient's core temperature and the patient's change in core temperature over time to a core temperature and a change in core temperature over time of a normal person at environmental temperatures monitored beginning with the temperatures included in said steep fall, and (d) means for issuing an alert if rise of core temperature of the patient from a temperature below a baseline temperature of the patient to a temperature at or closer to baseline lags behind rise of core temperature of the normal person from a temperature below a baseline temperature of the normal person to a temperature at or closer to baseline, or if the core temperature of the patient rises from a temperature below a baseline temperature of the patient to less than a predetermined minimum acceptable rise.

* * * * *